(12) United States Patent
Melsheimer

(10) Patent No.: US 8,241,250 B2
(45) Date of Patent: Aug. 14, 2012

(54) ROTATIONALLY ACTUATED FIXATION MECHANISM

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1382 days.

(21) Appl. No.: 11/846,870

(22) Filed: Aug. 29, 2007

(65) Prior Publication Data

US 2008/0058730 A1    Mar. 6, 2008

Related U.S. Application Data

(60) Provisional application No. 60/841,932, filed on Aug. 31, 2006.

(51) Int. Cl.
*A61M 29/00* (2006.01)
(52) U.S. Cl. .................. 604/105; 604/106; 604/177
(58) Field of Classification Search ............. 604/93.01, 604/95.03, 95.04, 107–109, 177, 523, 105, 604/106
See application file for complete search history.

(56) References Cited

U.S. PATENT DOCUMENTS

| | | | | |
|---|---|---|---|---|
| 1,719,428 | A | * | 7/1929 | Friedman ................. 604/105 |
| 1,870,942 | A | * | 8/1932 | Beatty ..................... 604/58 |
| 3,108,595 | A | | 10/1963 | Overment |
| 4,808,163 | A | * | 2/1989 | Laub ...................... 604/105 |
| 5,073,166 | A | | 12/1991 | Parks et al. |
| 5,232,440 | A | * | 8/1993 | Wilk ...................... 604/543 |
| 5,681,280 | A | | 10/1997 | Rusk et al. |
| 5,685,826 | A | * | 11/1997 | Bonutti ................... 600/204 |
| 5,716,325 | A | * | 2/1998 | Bonutti ................... 600/204 |
| 5,749,826 | A | | 5/1998 | Faulkner |
| 5,857,464 | A | * | 1/1999 | Desai ..................... 600/435 |
| 5,885,258 | A | * | 3/1999 | Sachdeva et al. ........... 604/530 |
| 6,014,579 | A | * | 1/2000 | Pomeranz et al. .......... 600/374 |
| 6,052,612 | A | | 4/2000 | Desai |
| 6,527,737 | B2 | | 3/2003 | Kaneshige |
| 6,569,150 | B2 | | 5/2003 | Teague et al. |
| 6,676,665 | B2 | * | 1/2004 | Foley et al. ............... 606/105 |
| 6,709,667 | B1 | | 3/2004 | Lowe et al. |
| 6,763,833 | B1 | | 7/2004 | Khera et al. |
| 6,764,519 | B2 | | 7/2004 | Whitmore |
| 6,979,321 | B2 | * | 12/2005 | Geis et al. ................. 604/181 |
| 2004/0199111 | A1 | * | 10/2004 | Gershowitz ............... 604/107 |
| 2006/0184192 | A1 | * | 8/2006 | Markworth et al. ......... 606/198 |
| 2006/0229553 | A1 | | 10/2006 | Hammack et al. |
| 2007/0167923 | A1 | | 7/2007 | Deal |

FOREIGN PATENT DOCUMENTS

WO     WO 98/15309     4/1998

OTHER PUBLICATIONS

International Search Report and Written Opinion for related PCT application No. PCT/US2007/018912, dated Jun. 2, 2008.

(Continued)

*Primary Examiner* — Nicholas Lucchesi
*Assistant Examiner* — Gerald Landry, II
(74) *Attorney, Agent, or Firm* — Brinks Hofer Gilson & Lione

(57) ABSTRACT

The present invention provides a gastrostomy or jejunal device for extended insertion into an abdomen of a patient. The device includes a catheter and a coaxial sheath that surrounds the catheter. The sheath includes a plurality of curved or oblique slots through the sheath materials that form a plurality of arms. A rotatable actuation device is provided to twist the sheath along its longitudinal axis which places the arms in compression and causes them to buckle radially outward beyond the circumference of the remainder of the sheath when the actuation device is rotated with respect to the remainder of the device.

22 Claims, 15 Drawing Sheets

OTHER PUBLICATIONS

Journal Article titled Percutaneous Gastrostomy and Gastrojejunostomy Tube Placement, Krishna Kandarpa and Kathleen Reagan, 2002 Copyright Date.

Cook Urological—Percutaneous Malecot Nephrostomy Sets, available at http://www.cookgroup.com/cook_urological/roducts/perc/4_04/4_04_04.html, printed Jan. 13, 2006.

* cited by examiner

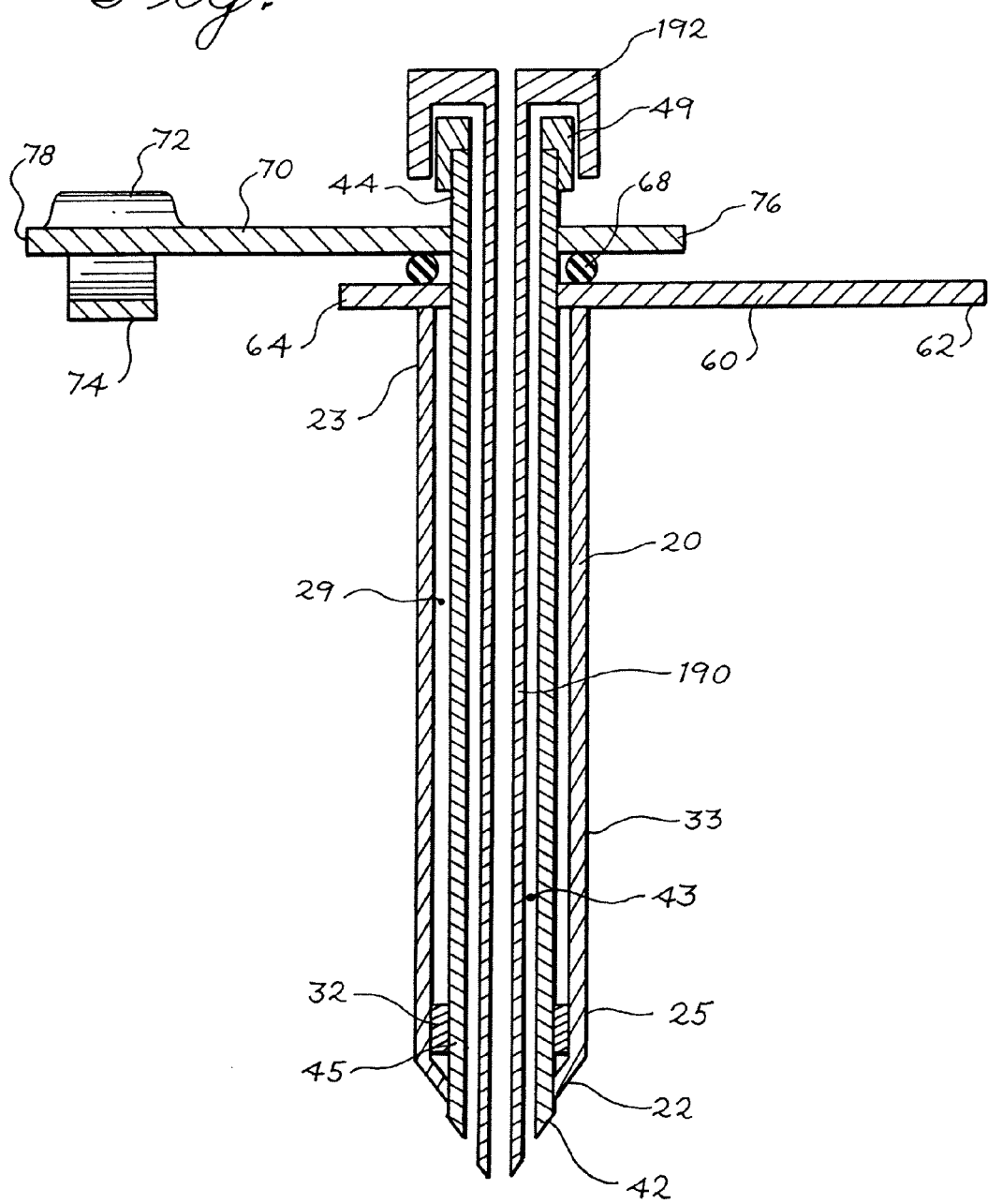

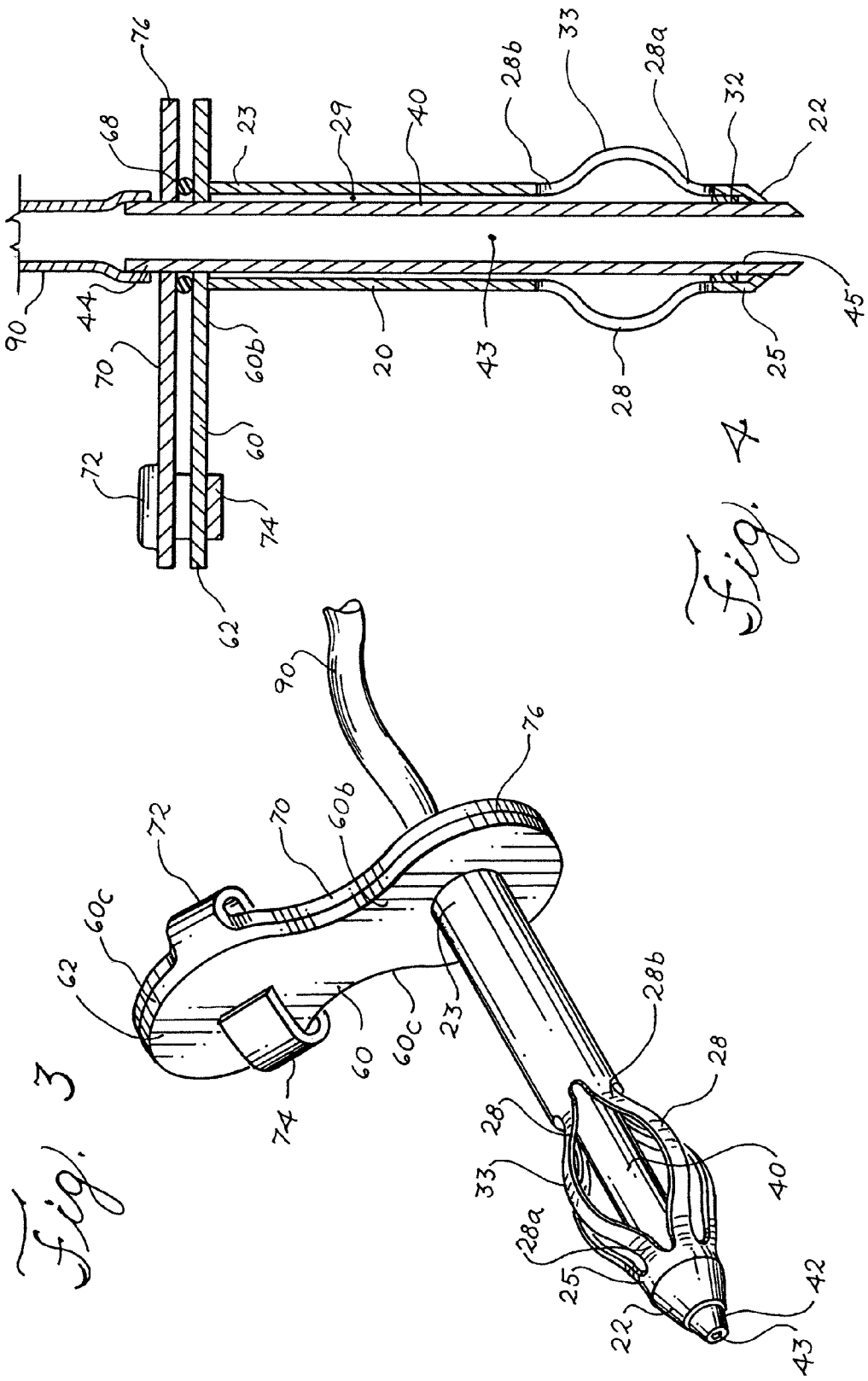

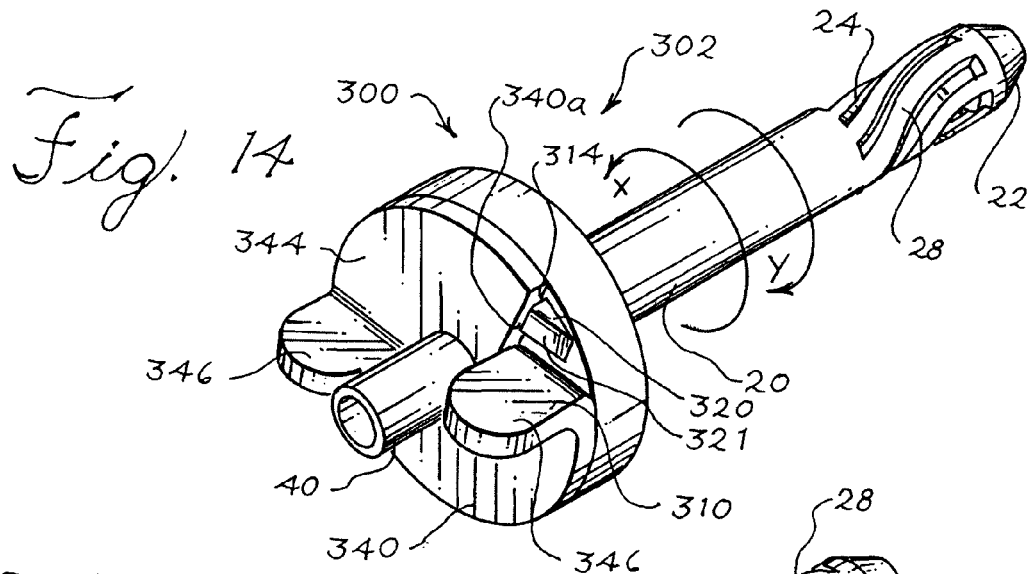
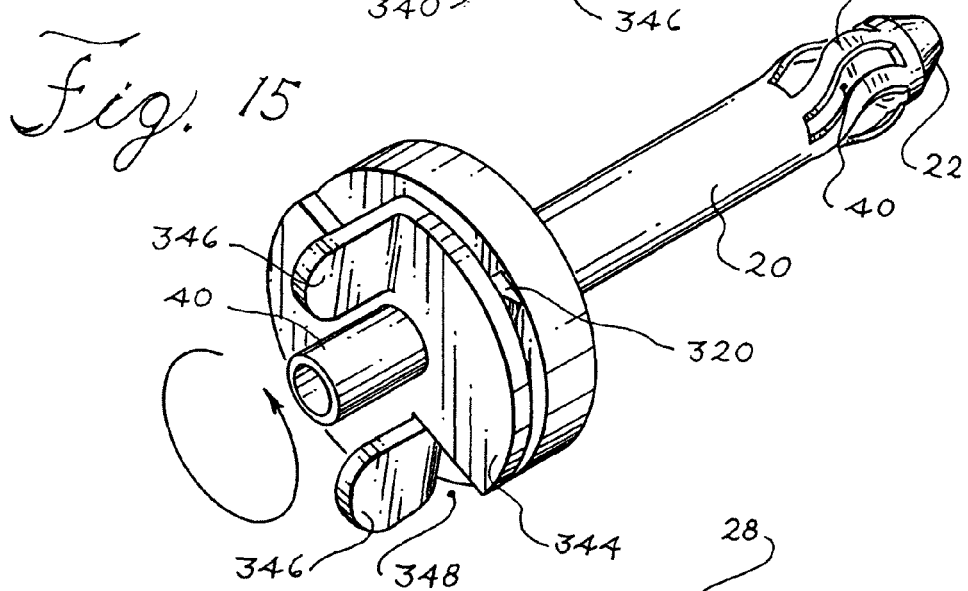
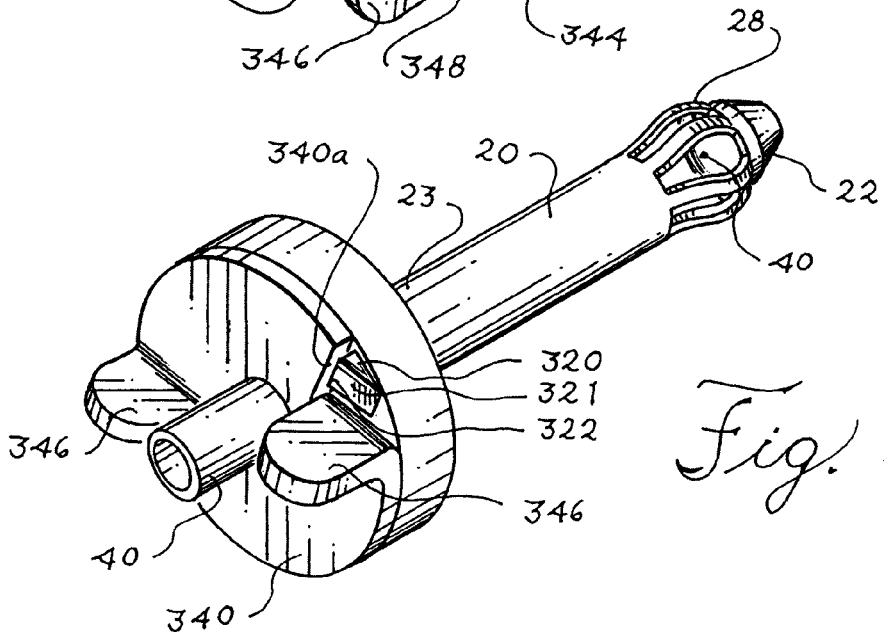

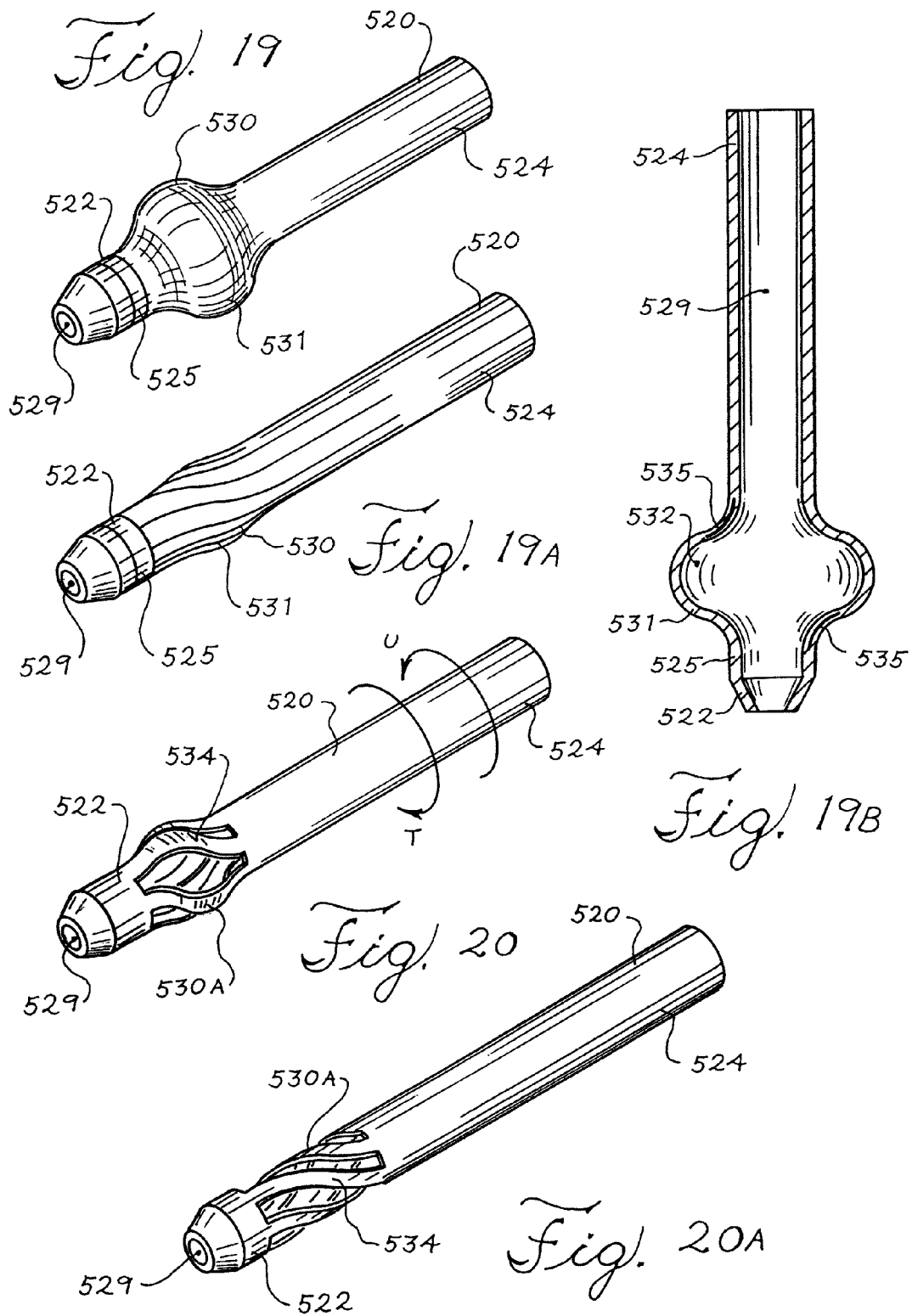

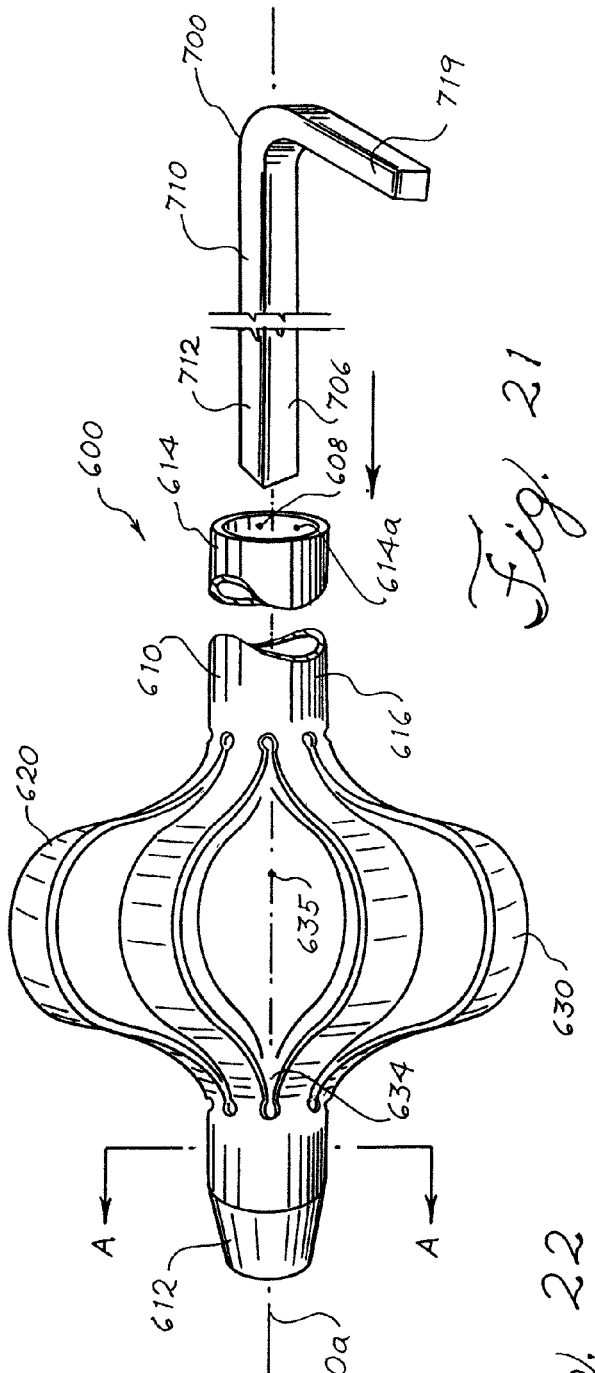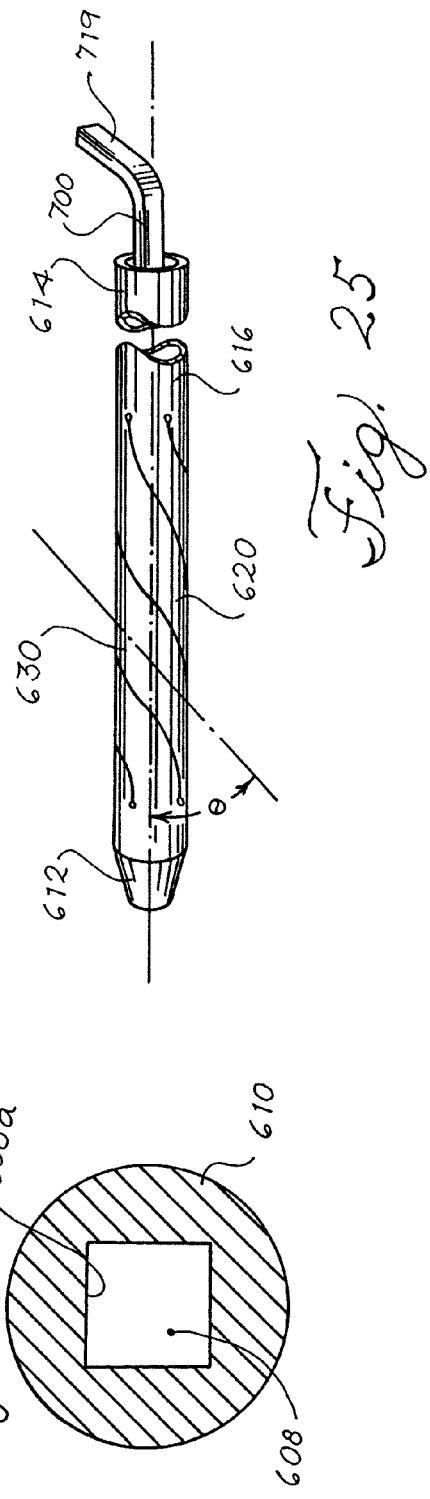

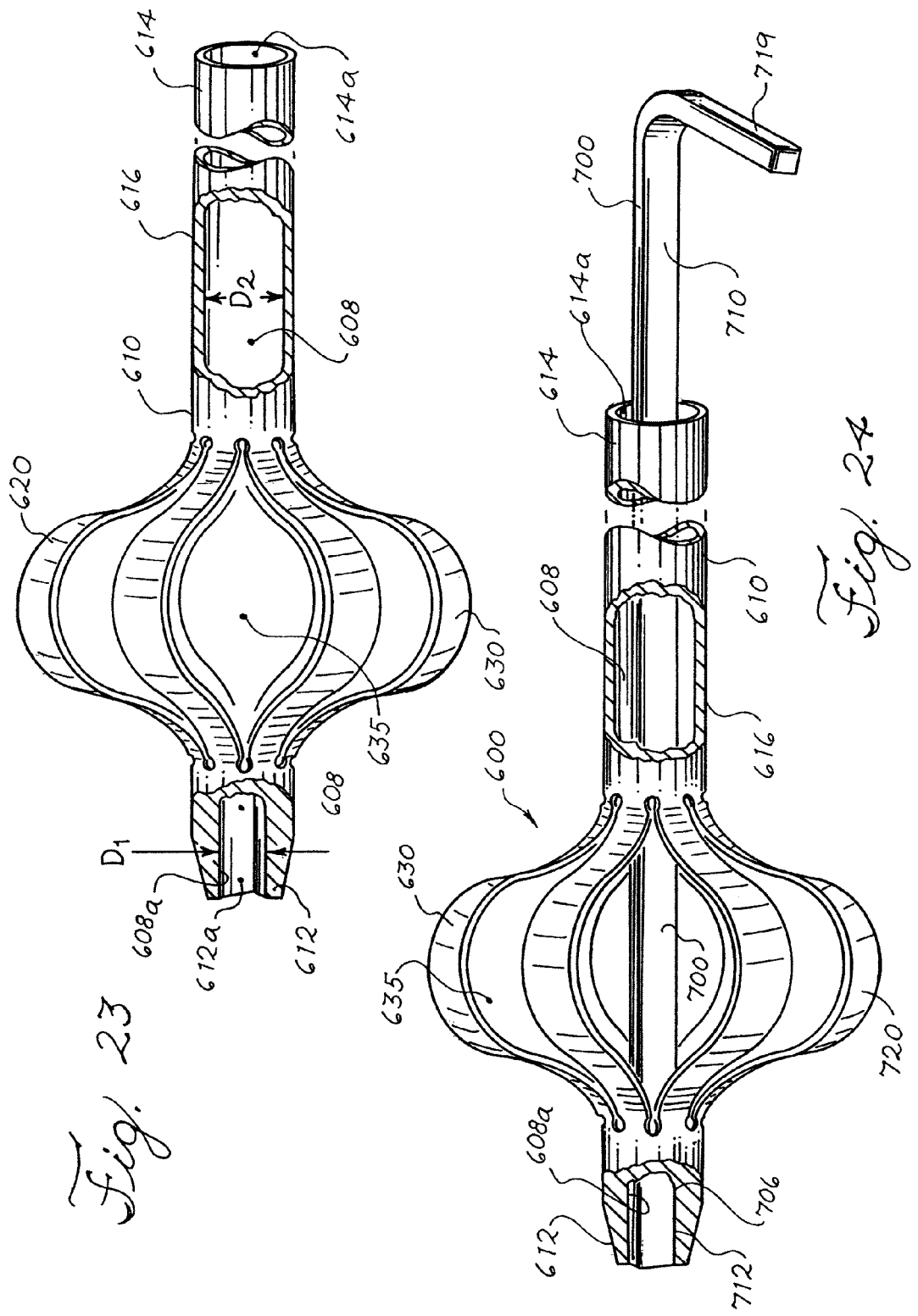

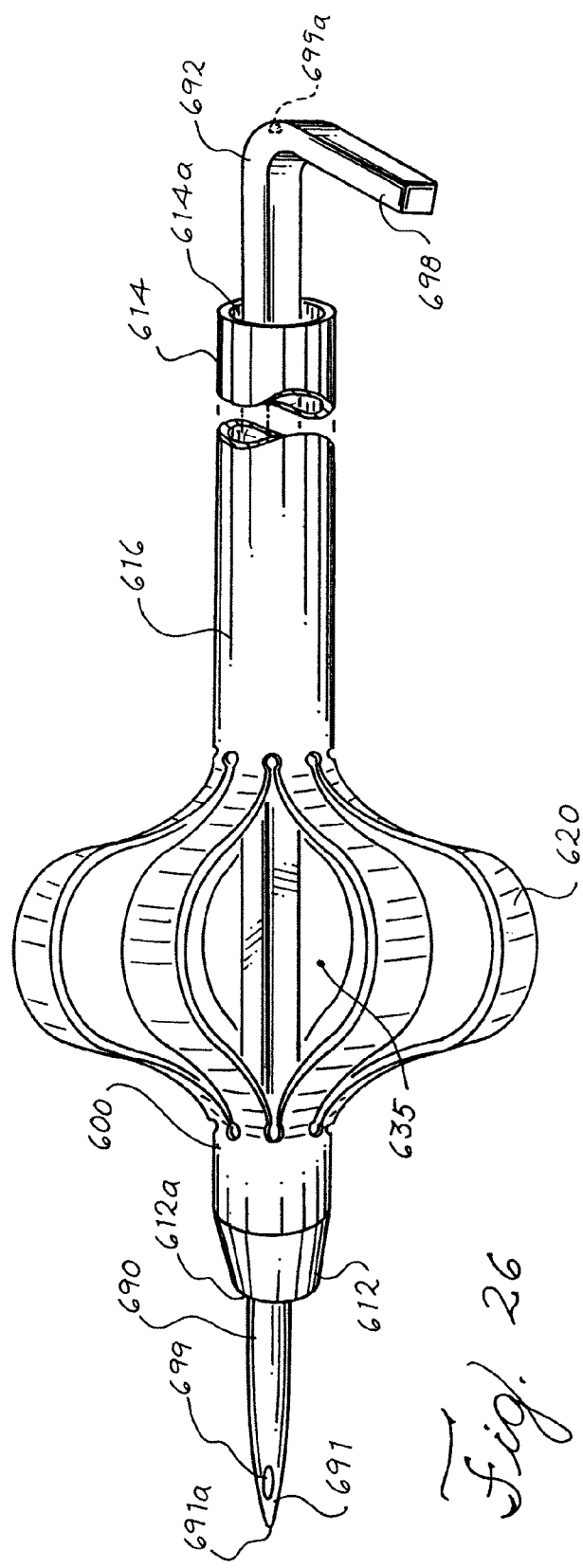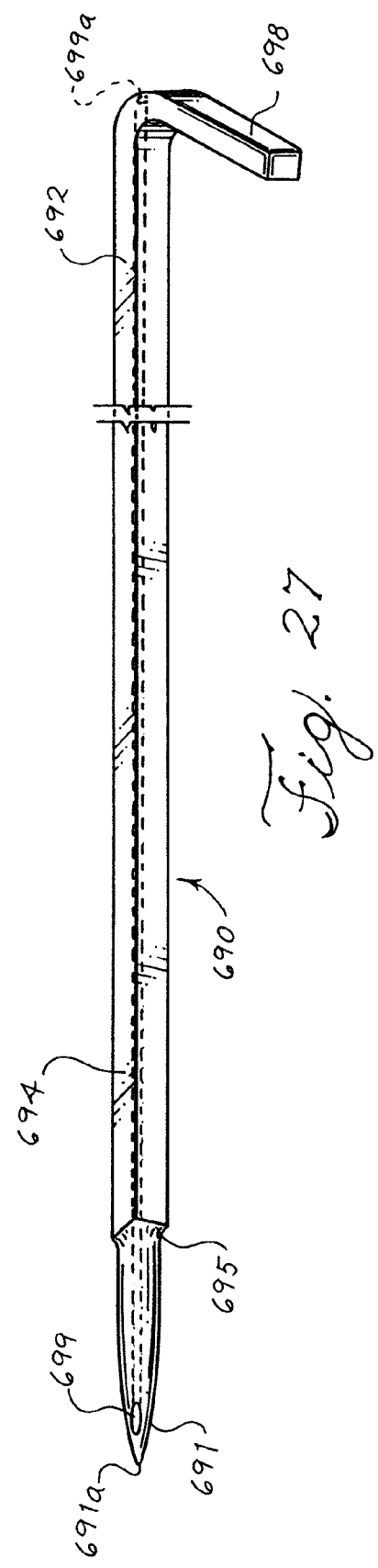

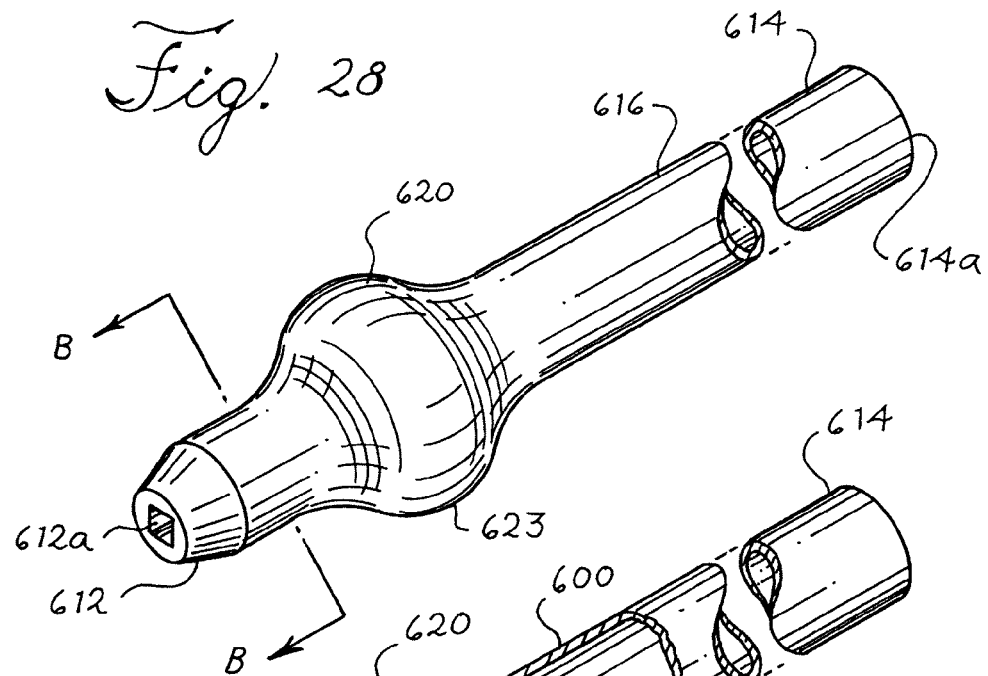
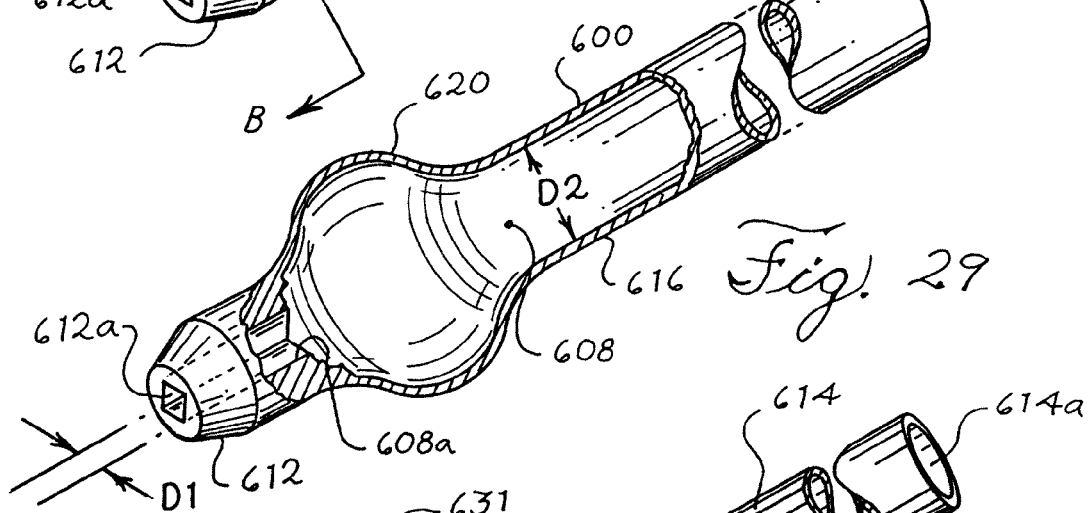
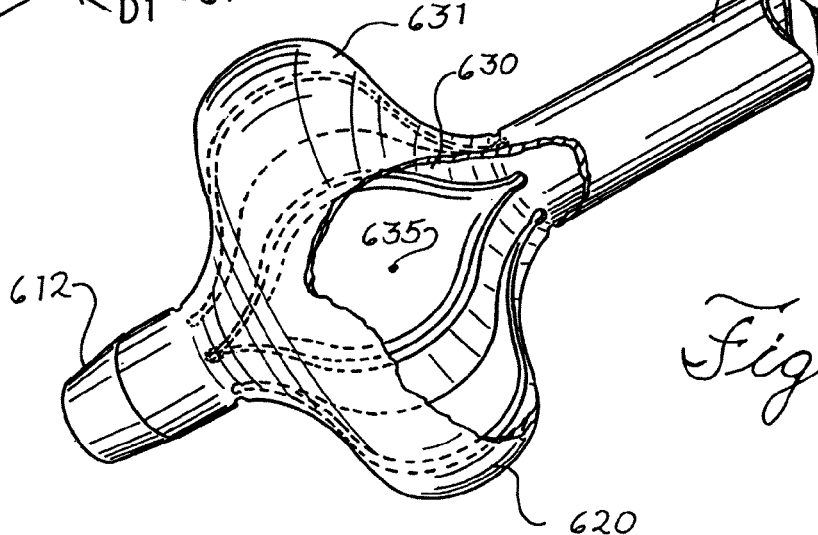

ROTATIONALLY ACTUATED FIXATION MECHANISM

CROSS-REFERENCE TO RELATED APPLICATIONS

This application claims priority from U.S. Provisional application No. 60/841,932, filed on Aug. 31, 2006, the entirety of which is fully incorporated by reference herein.

TECHNICAL FIELD

The present invention relates to percutaneously insertable gastrostomy or jejunal devices that may be inserted and retained within a patient for an extended period of time.

BACKGROUND

Often it becomes medically necessary to implant an external feeding tube (or a similar gastrostomy device) percutaneously into the gastrointestinal ("GI") tract through the patient's abdominal wall to provide the patient nourishment when the patient cannot receive food and liquid by the normal method of oral intake. This method of nourishment may be required for patients that suffer from neurological disorders, pulmonary disease, or head, neck, or esophageal lesions. In addition, nourishment directly to the patient's GI tract through the abdomen may be required when the patient exhibits decreased gastric motility, whether because of diabetic gastropathy, scleroderma, or other causes.

Because this substitute feeding method often must be employed in a patient for extended periods of time, it is desirable to implant a percutaneous device that provides direct communication with the GI tract. After a patient receives a device to allow long term feeding directly into their GI tract, the patient can resume at least some mobility and normal activity. When the patient requires nourishment, the patient can connect a source of nourishment directly to the extended end of the device to allow the nourishment to flow directly into the patient's GI tract.

It is known in the art to use a Foley type balloon catheter as the conduit to provide nourishment directly to a patient's GI tract. As is well known, a Foley balloon catheter includes an internal lumen that extends through the length of the catheter as well as an inflatable balloon near the distal end of the catheter. Accordingly, when the balloon is not inflated, the catheter maintains a low profile for convenient insertion into a patient. After the catheter is inserted and selectively positioned, the balloon may be inflated by inserting a fluid into the balloon, which increases the profile of the catheter to prevent it from being inadvertently withdrawn from the patient. It is a known disadvantage of Foley catheters that balloons may leak or catastrophically fail, which allows the balloon to shrink and the catheter to no longer be properly positioned within the patient. Accordingly, a Foley balloon catheter is often not suitable to be used as a long term percutaneous feeding device.

Alternatively, it is also known to use a catheter with a pigtail, or similar member, at the distal end to retain the catheter within the selected position within the patient. This type of catheter must be positioned within the patient with sutures, which may become loose or slip over time if the patient is even slightly active. Additionally, it is difficult for the medical professional to determine when the pigtail, or similar member, is properly installed within the patient.

Finally, it is also known to use a malecot tube with an internal lumen within the patient to provide the path for percutaneous feeding. As is known to those of ordinary skill in the art, malecot arms are normally at substantially the same profile as the remainder of the tube and are extendable when an internal member is pulled longitudinally toward the proximal end of the malecot tube. This longitudinal relative motion compresses the malecot tube, which buckles the malecot arms outwardly because the malecot arms provide the least resistance to compression. Because the malecot tube relies on longitudinal proximal movement of an internal member that is connected with a distal end of the malecot tube, the internal member maintains a relatively high profile, or extends a significant distance out of the proximal end of the malecot tube (which extends from the patient) to operate properly. This high profile may limit the activities that a patient can perform with a malecot tube installed.

Accordingly, it is desired to provide a device for percutaneous insertion into a patient's abdomen that overcomes the drawbacks of the prior art devices. Specifically, it is desired to provide a device that is appropriate for long term use, with the state of fixation being easily viewed, and maintains a low profile when the device is installed and fixed within the patient.

BRIEF SUMMARY

The present invention provides a medical device for use as a gastrostomy or a gastrojejunostomy feeding device. A medical device includes a substantially tubular hollow catheter having a distal end portion and a proximal end portion. A sheath is disposed coaxially about the catheter. The sheath includes a distal end portion and a proximal end portion, wherein the distal end portion of the sheath is substantially fixed to the catheter at a fixation point to prevent relative rotation between the catheter and the sheath at the fixation point. A bulge portion is defined in the sheath proximally of the fixation point, wherein rotation of the proximal end portion of the sheath relative to the proximal end portion of the catheter causes the bulge portion to move between a first configuration and a second configuration, the bulge portion forming a substantially larger circumference than the proximal end portion of the sheath in a first configuration and being substantially adjacent to the catheter in a second configuration.

The present invention additionally provides a percutaneous insertion device. A percutaneous insertion device includes a catheter with a distal end portion and a proximal end portion, a lumen disposed through the length of the catheter and a sheath with a distal end portion and a proximal end portion. The sheath is disposed coaxially with the catheter. The distal end portion of the sheath is substantially fixed to the distal end portion of the catheter at a fixation point. The sheath includes a plurality arms provided proximally of the fixation point. The sheath and the catheter are rotatable relative to each other proximally of the fixation point to cause the plurality of arms to extend radially outward.

A medical device is provided that includes a catheter with a distal end portion and a proximal end portion and a sheath with a distal end portion, a proximal end portion, and a central portion between the distal and proximal end portions. The sheath is disposed coaxially around the catheter with the distal end portions of the sheath and the catheter being substantially fixed together at a fixation point. The central portion is radially deformable between a first configuration and a second configuration, wherein in one of the first configuration and the second configuration the central portion is substantially adjacent to the catheter, and in the other of the first configuration and the second configuration the central portion is radially spaced away from the catheter.

A medical device is provided that includes a catheter defining a lumen between a distal end portion and a proximal end portion, wherein the distal end portion comprises a bulge portion that radially extends beyond an outer surface of a central portion of the catheter in an extended position. The bulge portion is configured to transfer to a narrowed position with substantially the same diameter as the outer surface of the central portion of the catheter when the catheter is twisted along a length of the catheter. A portion of the lumen within the distal end portion comprises a non-circular portion configured to be engaged by a mating portion of a member insertable through the lumen to accept relative rotation between the member and the catheter.

A medical device is provided that includes an elongate first member with a distal end portion, a central portion, a proximal end portion, and a lumen defined therethrough that includes a mating portion. A second member is coaxially positionable within the lumen of the first member and rigidly engageable with the mating portion. The first member additionally includes an expandable portion that is configured to translate between a first configuration where an outer diameter of the expandable portion is substantially the same as the outer diameter of the central portion of the catheter, and a second configuration where the outer diameter of the expandable portion is larger than the outer diameter of the central portion, wherein the expandable portion moves toward one of the first or the second configurations from the other of the first or the second configurations when the first member is rotated with respect to the second member with the second member is rigidly engaged with the mating portion.

Advantages of the present invention will become more apparent to those skilled in the art from the following description of the preferred embodiments of the invention that have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 2 is a cross-sectional view of the percutaneous insertion device of FIG. 1.

FIG. 3 is the view of FIG. 1 showing the percutaneous insertion device in a retention position.

FIG. 4 is a cross-sectional view of the percutaneous insertion device of FIG. 1 showing the device in a retention position.

FIG. 14 is a perspective view of fourth representative embodiment of a percutaneous insertion device, showing the device in the insertion position.

FIG. 15 is the view of FIG. 14 showing the device in an intermediate position.

FIG. 16 is the view of FIG. 14 showing the device in a retention position.

FIG. 19 is a perspective view of an alternate sheath in a retention position.

FIG. 19a is the sheath of FIG. 19 in an insertion position.

FIG. 19b is a cross-sectional view of the sheath of FIG. 19.

FIG. 20 is a perspective view of another alternate sheath in a retention position.

FIG. 20a is the sheath of FIG. 20 in an insertion position.

FIG. 21 is a perspective view of an alternate percutaneous insertion device showing a catheter and an operator exploded therefrom.

FIG. 22 is a cross-sectional view of FIG. 21 along section A-A.

FIG. 23 is partial cross-section view of the device of FIG. 21.

FIG. 24 is a perspective view of the device of FIG. 21 showing the catheter in the expanded position with the operator inserted within the catheter.

FIG. 25 is a perspective view of the device of FIG. 21 showing the catheter in the narrowed position.

FIG. 26 a perspective view of the device of FIG. 21 with an insertion dilator inserted therethrough.

FIG. 27 is a perspective view of the insertion dilator of FIG. 26.

FIG. 28 is a perspective view of another alternate percutaneous device.

FIG. 29 is a cross-sectional view of the device of FIG. 28.

FIG. 30 is a perspective view of an alternate percutaneous device showing a portion of the flexible cover removed.

DETAILED DESCRIPTION OF THE DRAWINGS AND THE PREFERRED EMBODIMENTS

Turning now to FIGS. 1-5, a first representative embodiment of a percutaneous insertion device 10 is provided. The device generally includes a catheter 40, a sheath 20 that substantially surrounds catheter 40, and an actuation member 60 that allows either of catheter 40 or sheath 20 to be rotated with respect to the other of catheter 40 or sheath 20.

Percutaneous insertion device 10 may be inserted into the patient's GI tract in accordance with conventional medical procedures. The patient may be a human or any other type of mammal. For example, during surgery the physician inserts an endoscope (not shown) or similar device through the patient's mouth or nose and into the patient's GI tract. The endoscope may be used to inflate the patient's stomach and to visualize the proper position for inserting the distal end of percutaneous insertion device 10. The physician inserts a needle and a guide wire percutaneously through the patient's abdominal wall to the position of the distal end of the endoscope. After the needle is removed, a series of dilators with increasing widths may be inserted and removed along the guide wire to increase the size of the hole, or stoma, to the outer diameter of percutaneous insertion device 10.

Figure 5:
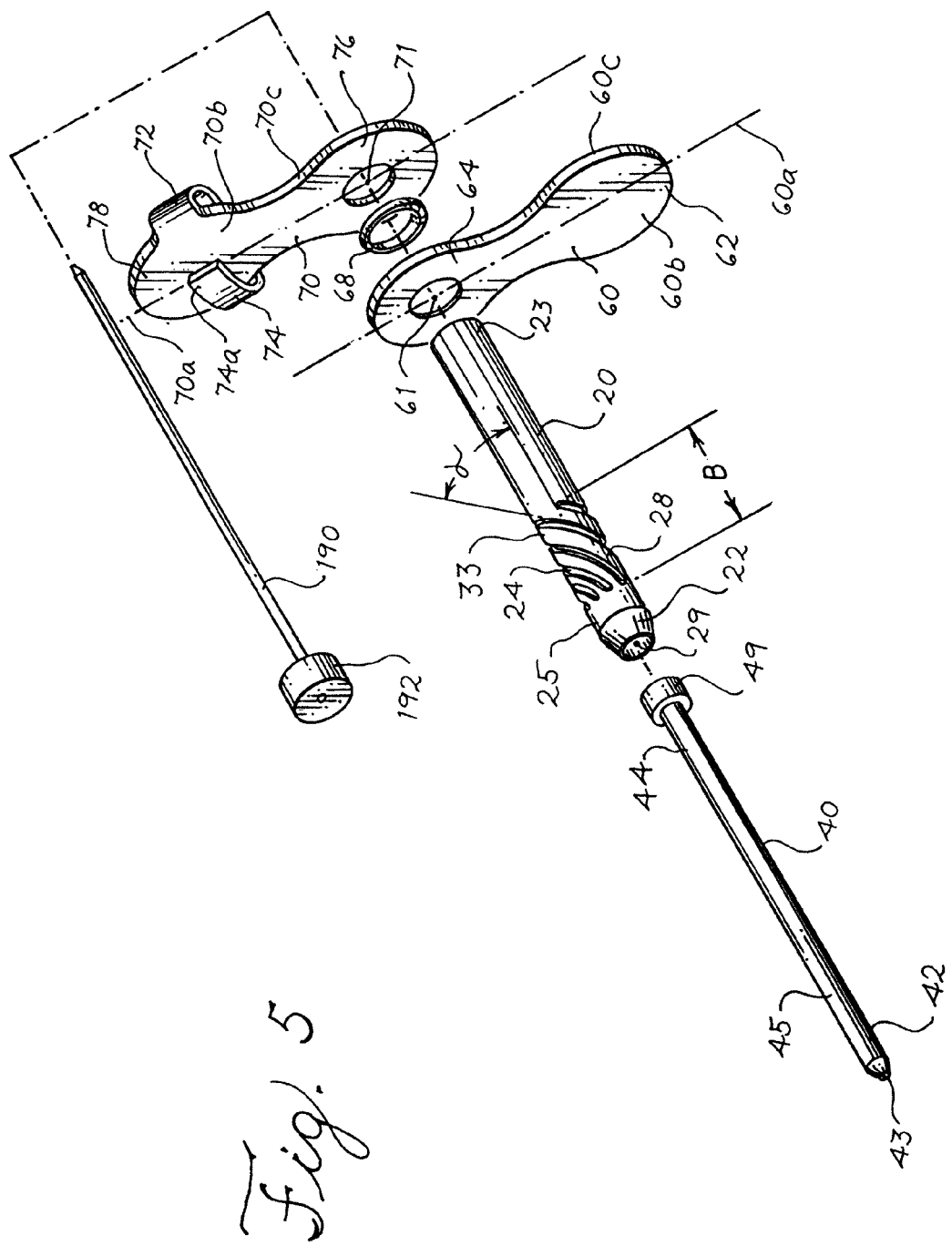
FIG. 5 is an exploded view of the components of the percutaneous insertion device of FIG. 1.
Figure 6:
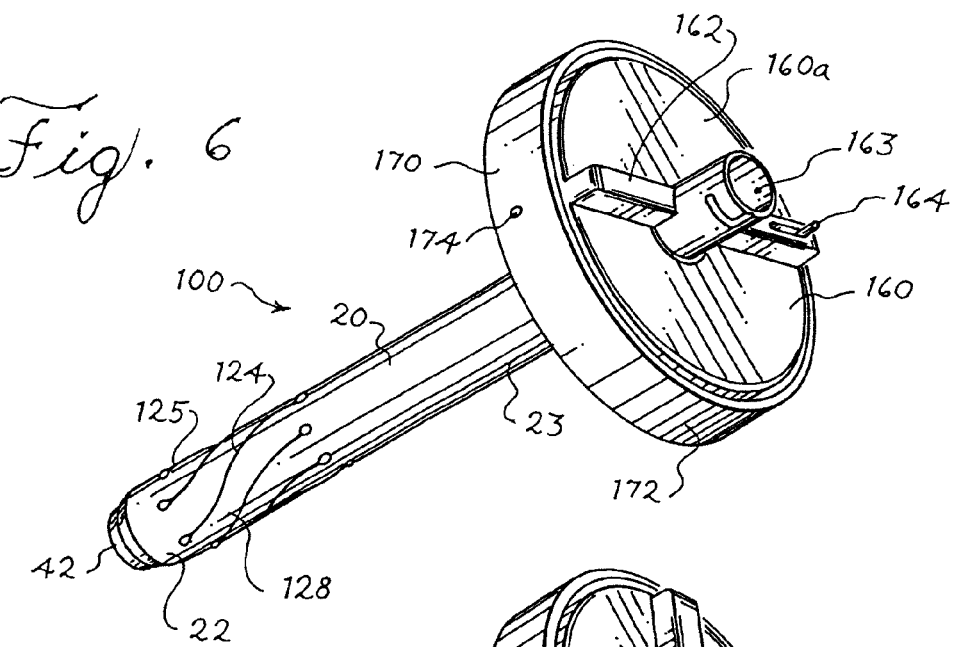
FIG. 6 is a perspective view of a second representative embodiment percutaneous insertion device showing the device in an insertion position.

Insertion dilator 190 is inserted through lumen 43 of catheter 40. The proximal end of the wire guide may be threaded through a lumen (not shown) in an insertion dilator 190 (FIGS. 2, 5). Percutaneous insertion device 10 and insertion dilator 190 are then inserted through the stoma along the wire guide until the arms 28 of sheath are positioned at the desired position within the patient. Once the percutaneous insertion device 10 is correctly positioned, the arms 28 are extended, as discussed below. The endoscope, insertion dilator 190, and the wire guide are then removed from the patient.

Sheath 20 may include a plurality of slots 24 that extend at least along a portion of the length of sheath 20. A tube 90 may be connected to a proximal end portion 44 of catheter 40 to provide a flow path for receiving liquid flowing through lumen 43 of catheter 40 into the patient, or to provide a flow path for providing liquid into lumen 43 of catheter 40 that flows out of a distal end portion 42 of catheter 40 from the patient.

Sheath 20 may be formed from a sufficiently flexible but strong material such as silicone, polyurethane, or known co-polymers of these materials, such that sheath 20 may be twisted along the longitudinal axis 21 (shown in FIG. 5) of sheath 20. Sheath 20 is provided with a distal end portion 22 and a proximal end portion 23. As best understood with reference to FIGS. 2 and 4, sheath 20 includes a lumen 29 along the length of sheath with an internal diameter slightly larger than the outer diameter of catheter 40. Distal end portion 22 of sheath 20 may be formed as a truncated cone with the inner diameter of the distal end of the cone being substantially the same as the outer diameter of distal end portion 42 of catheter 40. Sheath 20 includes a fixation region 25 on, or just rearward of, distal end portion 22 of sheath 20 and in the proximity of the forward ends 26 of the plurality of slots 24.

Figure 1:
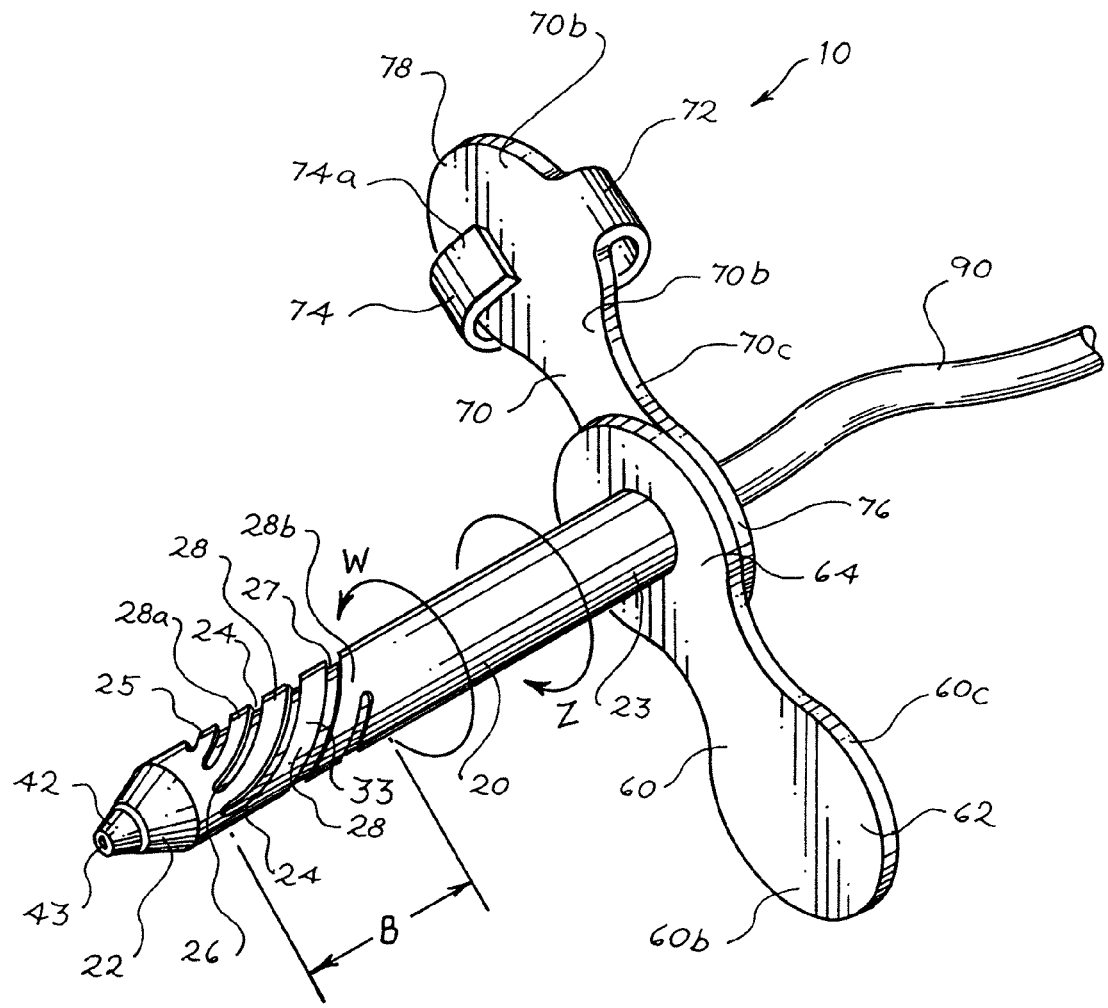
FIG. 1 is a perspective view of a first representative embodiment of a percutaneous insertion device showing the device in an insertion position.

As best shown in FIG. 1, the plurality of slots 24 are formed in sheath 20. The plurality of slots 24 are provided in the vicinity of distal end portion 22 of sheath 20 and each slot 24 extends along a portion of the length of sheath 20 toward proximal end portion 23 of sheath 20. Slots 24 are formed through the entire material thickness of sheath 20. Each slot 24 is arranged in parallel with the adjacent slots 24 along the circumference of the sheath 20 and at an oblique angle with respect to the longitudinal axis 21 of sheath 20. Each forward end 26 of slot 24 is located the same distance rearward of fixation region 25 of sheath 20, and each rear end 27 of slots 24 is similarly formed at the same longer distance rearward of fixation region 25 of sheath 20. Accordingly, as discussed above, all slots 24 are arranged to be parallel to adjacent slots 24. In addition, all slots are the same length and slots 24 are arranged at consistent intervals (or arc lengths) between adjacent slots around the circumference of sheath 20.

Slots 24 may be curved along their length between the forward and rear ends 26, 27, such that the angle a (shown in FIG. 5) between slot 24 and longitudinal axis 21 changes along the length of slots 24. In other embodiments, slots 24 may be formed such that the angle a is a constant angle along the length of slots 24 (when device 10 is in the position shown in FIG. 1).

The portions of sheath 20 located between the plurality of slots 24 define a plurality of arms 28. Arms and slots 28, 24 are provided in a central portion 33 of sheath 20 between the distal end portion 22 and the proximal end portion 23. When device 10 is positioned as shown in FIGS. 1-2, the circumference of arms 28 and slots 24 is substantially the same as the circumference of proximal end portion 23 of sheath 20. Specifically, the plurality of arms 28 and slots 24 are substantially the same nominal circumference as the proximal end portion 23 of sheath 20. In other embodiments, slots 24 may be replaced with regions of relatively elastic material provided between neighboring arms 28, such as an elastomeric polymer. The elastic material is provided to significantly stretch when arms 28 extend radially outward as sheath 20 and catheter 40 are rotated with respect to each other, as discussed below.

Arms 28 extend beyond the outer circumference of proximal end portion 23 of sheath 20 when the insertion device 10 is placed in a retention position, shown in FIGS. 3-4. Accordingly, arms 28 operate similarly to the arms of a malecot device that is known to those of ordinary skill in the art, in that device 10 can be positioned between a profile in which arms 28 and proximal end portion 23 of sheath 20 have substantially the same circumference, with arms substantially adjacent to catheter 40, to a profile in which arms 28 are extended with a substantially larger circumference than the circumference of proximal end portion 23 of sheath 20. Specifically, the nominal circumference of arms 28 becomes substantially larger than the nominal circumference of proximal end portion 23 of sheath.

Arms 28 each include a forward end 28a and a rear end 28b. Because slots 24 are formed at oblique angles to longitudinal axis 21 of sheath 20, a first distance measured between forward and rear ends 28a, 28b of a single arm 28 (i.e. the full length of a single arm 28) is greater than a second distance B (FIG. 1) measured along the longitudinal axis 21 between the collective forward ends 28a of arms 28 and the collective rear ends 28b of arms 28. Accordingly, when sheath 20 is placed in torsion (as discussed below), arms 28 are untwisted or unwound until each arm 28 is substantially parallel to longitudinal axis 21. Because each arm 28 is longer (i.e. the distance between forward end and rear end 28a, 28b of each specific arm 28) than the distance B between the collective forward and rear ends 28a, 28b of arms 28, arms 28 are compressed and buckle to form an "arch" or a parabola with a mid section that extends radially beyond the outer diameter of the proximal end portion 23 of sheath 20 (as best shown in FIG. 3) and away from catheter 40 when sheath 20 and catheter 40 are rotated with respect to each other, as discussed below. When the torque causing the relative rotation is released, arms 28 relax toward the orientation shown in FIG. 1 because the compressive force applied to arms 28 that caused them to buckle, is released.

Catheter 40 includes a distal end portion 42 and a proximal end portion 44 with a lumen 43 provided through the length of catheter 40. Sheath 20 is preferably formed from a relatively stiffer material than that used to form catheter 40. In some embodiments polyurethane may be used to form catheter 40. Catheter 40 includes a fixation region 45 on, or slightly proximally of, distal end portion 42 of catheter 40. When catheter 40 is connected to sheath 20, fixation region 45 of catheter 40 and fixation region 25 of sheath 20 are positioned concentrically with each other and are substantially fixed such that sheath 20 and catheter 40 are substantially prevented from rotating with respect to each other at the point of attachment between the two fixation regions 25, 45.

In embodiments using an insertion dilator 190, proximal end portion 44 of catheter 40 may include a connector 49 fixed to proximal end portion 44 that is engageable with a corresponding connector 192 on insertion dilator 190 to connect catheter 40 and insertion dilator 190 when insertion dilator 190 is inserted through lumen 43 of catheter 40 (FIGS. 2 and 5). Connectors 49 and 192 may each include corresponding screw threads, or may be removeably engageable with other structures known in the art.

The two fixation regions 25, 45 may be connected together by heat bonding the two regions. Alternatively, as shown in FIGS. 2 and 4, the two fixation regions 25, 45 may be fixed together with an adhesive 32 or a solvent bond. As understood by those of ordinary skill in the art, the materials used for sheath 20 and catheter 40 must be such that the two materials are capable of being heat bonded together, or that they can each be rigidly mounted together with an adhesive 32. Further, fixation region 25 of sheath 20 and fixation region 45 of catheter 40 may be rigidly connected by crimping the two components together. In other embodiments, catheter 40 and sheath 20 may be connected together at their relative fixation regions 45, 25 using other methods that are known to those of ordinary skill in the art. For example, in some embodiments when sheath 20 and catheter 40 are crimped together (or when using any other procedure for connecting these components together) a mandrel (not shown) may be inserted through lumen 43 on distal end portion 42 of catheter 40 to support the inner diameter of fixation region 45, such that lumen 43 maintains a sufficient cross-sectional area for flow.

As shown FIGS. 19-20a, an alternate sheath 520 may be provided on percutaneous insertion device 10. Other than the differences noted below, sheath 520 operates similarly to sheath 20 discussed herein and is engaged with a catheter 40 that is similar to those discussed herein. Sheath 520 and catheter 40 may be suitably adapted to be used with any of the actuation mechanisms or locking mechanisms discussed herein.

Sheath 520 includes a distal end portion 522, a proximal end portion 524, and a lumen 529 that extends through the length of sheath 520 with an internal diameter slightly larger than the outer diameter of catheter 40. Catheter 40 is provided coaxially within lumen 529 of sheath 520. Sheath 520 includes a fixation region 525 on, or just rearward of, distal end portion 522. Similar to the embodiment discussed above, fixation region 525 of sheath 520 and fixation region 45 of catheter 40 are positioned concentrically with each other and are substantially fixed such that sheath 520 and catheter 40 are substantially prevented from rotating with respect each other at the fixation point between the two fixation regions 525, 45. Sheath 520 and catheter 40 may be substantially fixed together using the methods discussed above.

Sheath 520 includes a bulge portion 530 (530a) that is provided rearward of fixation region 525. Bulge portion 530 may be formed with a substantially continuous outer surface around the circumference of the bulge portion 530 that is biased radially beyond the outer circumference of second end portion 524 of sheath 520 away from the proximity of catheter 40. As shown in FIGS. 19, 19a, and 19b, bulge portion 530 includes an outer surface 531 that encloses a substantially hollow interior portion 532. Alternatively, as shown in FIGS. 20 and 20a, an alternate bulge portion 530a may be formed with a plurality of parabolic arms 534 that are biased to extend radially outward from the circumference of second end portion of sheath 520, or away from the proximity of catheter 40.

Bulge portion 530 (530a) may include a plurality of springs 535 that are normally biased to radially extend bulge portion 530 beyond the circumference of proximal end portion 524 of sheath 520. Alternatively, bulge portion 530 may be formed with a naturally resilient material and shaped to be naturally biased outward away from catheter 40. In other embodiments, bulge portion 530 may be formed with other geometries that are biased outward from the remaining outer circumference of sheath 520.

In operation, as sheath 520 and catheter 40 are rotated with respect to each other proximally of the respective fixation points 525, 45, bulge portion 530 (530a) narrows, or compresses, toward the circumference of second end portion 524 of sheath 520 and substantially adjacent to catheter 40. Specifically, as sheath 520 and catheter 40 are rotated with respect to each other, the majority of the torque on sheath 520 is carded by bulge portion 530, which lengthens and elongates as it is twisted. As bulge portion 530 lengthens and elongates, the circumference or periphery of the bulge portion 530 is correspondingly reduced toward the circumference of second end portion 524 of sheath 520 and toward catheter 40. In order to concentrate the torsional stress due to the relative rotation of sheath 520 and catheter, bulge portion 530 may be formed from a thinner material than remaining portions of sheath 520. Alternatively, bulge portion 530 may be formed with a relatively weaker material than the remaining portions of sheath 520.

In embodiments where bulge portion 530 is formed with the substantially continuous outer surface, the sheath 520 and catheter 40 may be rotated with respect to each other in either rotational direction, which causes bulge section 530 to twist, which reduces the circumference of bulge portion 530 until it is substantially the same as the circumference of proximal end 523 of sheath 520 (as shown in FIG. 19a). In embodiments where bulge portion 530a includes a plurality of arms 534, sheath 520 is rotated with respect to catheter 40 in direction T (FIG. 20) to provide additional twist on arms 534, which causes the circumference of bulge portion 530a until it is substantially the same as the circumference of proximal end 523 of sheath 520. When the relative rotation between sheath 520 and catheter 40 is released, bulge portion 530 (530a) relaxes toward the normal extended, or retention position due to the outward biasing force of bulge portion 530. Specifically, as sheath 520 and catheter 40 are released, sheath 520 rotates with respect to catheter in direction U (FIG. 20) in embodiments that include bulge portion 530a, and sheath 520 rotates relative to catheter 40 in the opposite direction from the twisting direction in embodiments with bulge portion 530.

Because the outer circumference of bulge section 530 is reduced when sheath 520 and catheter 40 are rotated with respect to each other, device 10 is suitable for being inserted into a patient in the rotated, or insertion position. After device 10 is properly inserted and correctly positioned, the relative rotation between sheath 520 and catheter 40 can be released. As the relative rotation between 520 and catheter 40 is released, bulge portion 530 returns to original orientation due to the outward biasing force of bulge section 530, which allows device 10 to be retained in the selected position within the patient due to contact between neighboring organs of the patient and the bulge portion 530.

Returning now to FIGS. 1-5, actuation member 60 may be connected to proximal end portion 23 of sheath 20 such that rotation of actuation member 60 causes similar rotation of sheath 20. As shown in FIG. 1, actuation member 60 may be formed as a handle with a pivot end 64 formed with an aperture 61 (FIG. 5) that accepts proximal end portion 23 of sheath 20. Actuation member 60 also includes an extended end 62 that may be held and manipulated by the user, In a preferred embodiment, a longitudinal axis 60a (FIG. 5) of actuation member 60, which extends through both pivot and extended ends 64, 62 is perpendicular to longitudinal axis 21 of sheath 20.

Actuation member 60 may be formed with substantially flat front side 60b and rear side (not shown) surfaces and a thin curved edge surface 60c around the circumference of actuation member 60. As shown in FIG. 1, actuation member 60 may include an ergonomic, curved profile to readily be manipulated by the user. In other embodiments, actuation member 60 may be formed in other shapes that allow actuation member 60 to be readily and ergonomically manipulated by the user. Actuation member 60 and sheath 20 are preferably substantially rigidly connected together such that rotation of actuation member 60 causes similar rotation of sheath 20.

Percutaneous insertion device 10 may additionally include a receiving member 70. As shown in FIGS. 2 and 4, receiving member 70 may be substantially rigidly mounted to proximal end portion 44 of catheter 40. Receiving member 70 may be formed as a second handle. As shown in FIG. 1, receiving member 70 may be formed as a handle with a pivot end 76 formed with an aperture 71 (FIG. 5) that accepts proximal end portion 44 of catheter 40. Receiving member 70 additionally includes an extended end 78 that may be held by the user. In a preferred embodiment, a longitudinal axis 70a (FIG. 5) of receiving member 70 extends through both pivot and extended ends 76, 78 and is perpendicular to longitudinal axis 21 of sheath 20. In some embodiments (as shown in FIGS. 2, 4, and 5), an o-ring 68 may be provided between actuation member 60 and receiving member 70 to minimize the frictional contact between the two components. O-ring 68 additionally acts as a seal to minimize the leakage of liquid or gas within the device 10 from leaking out, and minimizes liquid or gas from outside device 10 to flowing into device 10.

As shown in FIG. 1 receiving member 70 may be formed with substantially flat front side 70b and rear side (not shown) surfaces and with a thin curved edge surface 70c around the circumference of receiving member 70. Receiving member 70 may include an ergonomic, curved profile to readily be manipulated by the user. In other embodiments, receiving member 70 may be formed in other shapes that allow receiving member 70 to be readily manipulated by the user. As shown in FIGS. 1-4, receiving member 70 may additionally include a latch 74 that extends from extended end 78. Latch 74 may extend from a portion of the edge surface 70b and curves toward front side surface 70b. Latch 74 is preferably formed to be at least slightly flexible. An extended end 74a of latch 74 is in close proximity to the front side surface 70b of receiving member 70 such that the distance between the two components is less than the width of the actuation member 60. Receiving member 70 may also include a hook 72 to retain the gastrostomy tube 90 to minimize the profile of device 10 that extends from the patient.

Percutaneous insertion device 10 is biased toward an insertion position, as shown in FIGS. 1-2, but may be manipulated to place and retain the device in a retention position, as shown in FIGS. 3-4. In some embodiments, when device 10 is in the insertion position, actuation member 60 extends from sheath 20 in substantially the opposite direction that receiving member 70 extends from catheter 40. When it is desired to manipulate the device 10 to position it in the retention position, the user holds receiving member 70 and rotates actuation member 60 in the direction Z (as shown in FIG. 1) toward receiving member 70. Alternatively, receiving member 70 may be rotated in direction W with respect to actuation member 60. As actuation member 60 and receiving member 70 are rotated toward each other, fixation regions 25, 45 substantially prevent relative rotation between sheath and catheter 20, 40 at fixation regions 25, 45. Accordingly, the torque created by the relative rotation of actuation and receiving members 60, 70 is applied to either sheath 20 or catheter 40 proximally of the respective fixation regions 25, 45. Sheath 20 is preferably formed from a material with substantially the same stiffness as catheter 40.

Because arms 28 are the weakest portions of sheath 20, the majority of the torque carried by sheath 20 is localized within the arms 28, causing arms 28 to twist. This twisting moves arms 28 toward an orientation parallel with longitudinal axis 21. As discussed above, because arms 28 are longer than distance B (shown on FIG. 1), a compressive force is applied to arms 28 when arms 28 are twisted toward an orientation parallel with longitudinal axis 21. Due to the applied compressive force, arms 28 buckle, or deflect, outward to form an arch with a middle portion that extends radially from the outer diameter of sheath 20 (as shown in FIGS. 3 and 4).

As actuation member 60 approaches receiving member 70, curved edge 60c and rear side surface 60b contact latch 74. Because both latch 74 and actuation member 60 are slightly flexible, the two members flex to allow the latch 74 to pass behind actuation member 60. With sufficient rotation, actuation member 60 passes free of latch 74 and is positioned with respect to receiving member 70 as shown in FIG. 3. Latch 74 contacts curved edge 60c of actuation member 60 and prevents actuation member 60 from rotating toward the orientation shown in FIG. 1 due to the biasing force of the twisted sheath 20 and the buckled arms 28. Accordingly, device 10 may be maintained in the retention position shown in FIG. 3.

When the user desires to transfer device 10 back to the insertion position (to allow device 10 to be removed from patient), the user rotates actuation member 60 with respect to receiving member 70 further in the Z direction until it is no longer contacted by latch 74. By flexing both actuation member 60 and latch 74, actuation member 60 may rotate in the W direction over latch 74 and toward the insertion position shown in FIG. 1. As can be understood, twisted sheath 20 and catheter 40 and buckled arms 28 provide a biasing force to rotate actuation member 60 toward the insertion position. Additionally, as the sheath 20 relaxes (with rotation of the actuation member 60), arms 28 and slots 24 regain their oblique (and in some embodiments curved) profile with respect to longitudinal axis 21 of sheath 20, and the arch lowers until the circumference of arms 28 and slots 24 is substantially the same as proximal end portion 23 of sheath 20.

Turning now to FIGS. 6-10, a second representative embodiment of a percutaneous insertion device 100 is provided. This embodiment includes sheath 20, catheter 40, and arms 28 on sheath 20, which operate based on relative rotation between sheath 20 and catheter 40. Alternatively, sheath 520 with bulge portion 530 (530a), as discussed above, may be provided on device 100. As with the embodiments discussed above, catheter 40 and sheath 20 are fixed together at respective fastening regions 25, 45, allowing sheath 20 and catheter 40 to be rotated with respect to each other proximally of the respective fixation regions 25, 45. The sheath 20 and catheter 40 are formed and connected in the same way as discussed with respect to the first representative embodiment 10 above, and for the sake of brevity will not be repeated here.

An actuation member 160 is provided that extends from a proximal end portion 44 of catheter 40. In other embodiments, the actuation member may be constructed to extend from a proximal end portion of sheath 20. Actuation member 160 is formed as a disk that is rigidly mounted to the proximal end portion 44 of catheter 40. Actuation member 160 includes an aperture 163 through its center which allows fluid communication between the aperture 163 and the lumen 43 within catheter 40. Actuation member 160 includes a handle 162 that extends from a side surface 160a of actuation member 160. Handle 162 provides a projection for the user to grip and rotate actuation member 160.

A receiving drum 170 is provided that is rigidly connected to the proximal end 23 of sheath 20. Receiving drum 170 includes a flat section that is connected with the proximal end portion 23 of sheath 20 and includes an aperture to allow catheter 40 to pass through. A round and hollow annulus 172 extends rearwardly of the flat section and includes an internal open volume that accepts actuation member 160. The inner diameter of annulus 172 is slightly larger than the outer diameter of actuation member 160 such that actuation member 160 can freely rotate with respect to receiving drum 170.

Figure 9:
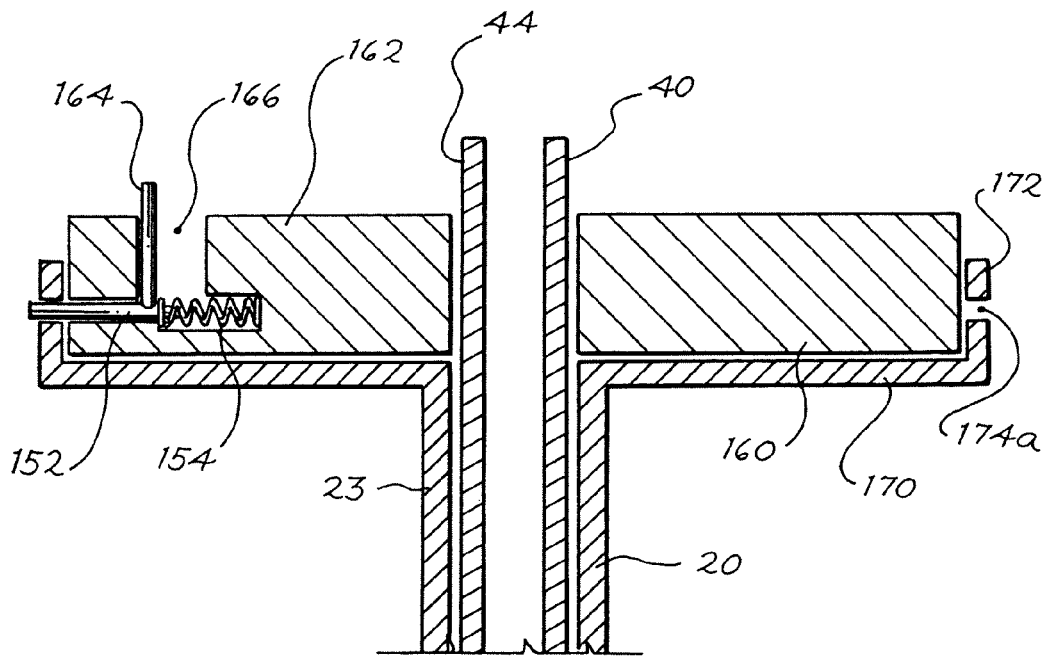
FIG. 9 is a cross-sectional view of the locking device of FIG. 6, in a locked position.

As shown in FIGS. 6-10, annulus 172 may include at least one aperture 174. Aperture 174 selectively receives a pin 152 that is radially extendable from the curved side surface of actuation member 160. In some embodiments, a lever 164 is provided on handle 162 (or another suitable portion of actuation member 160), which may be operated to selectively move pin 152 with respect to the curved side surface of actuation member 160. As shown in FIG. 9, when device 100 is in the retention position (i.e. with arms 28 extending radially outward from the remainder of sheath 20), pin 152 may be extended through aperture 174 to retain device 100 in the retention position. Device 100 can be repositioned in the insertion position (shown in FIG. 6) by withdrawing pin 152 from aperture 174. In some embodiments, a second aperture 174a may be provided to receive pin 152 and retain device 100 in the insertion position.

Figure 7:
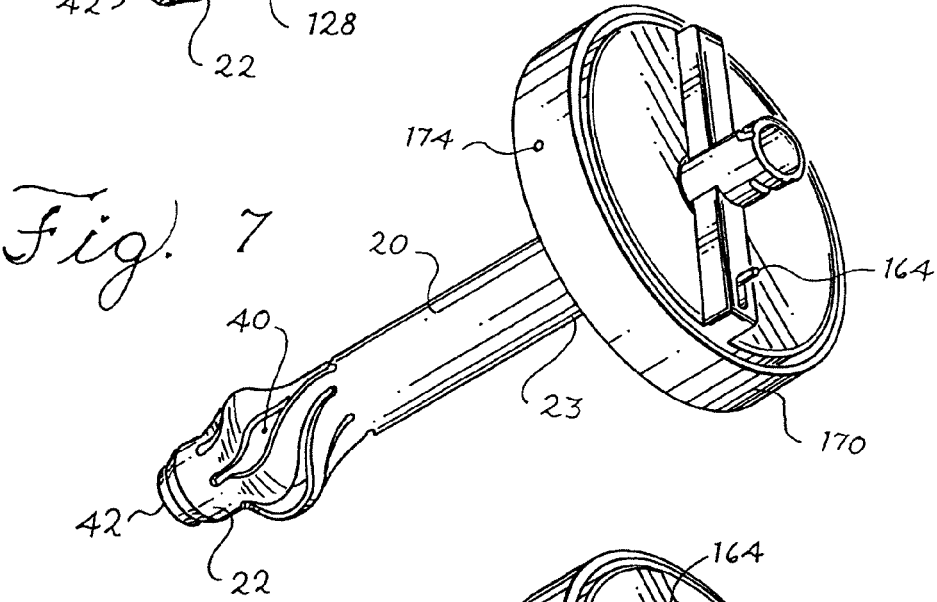
FIG. 7 is the view of FIG. 6 showing the device in an intermediate position.
Figure 8:
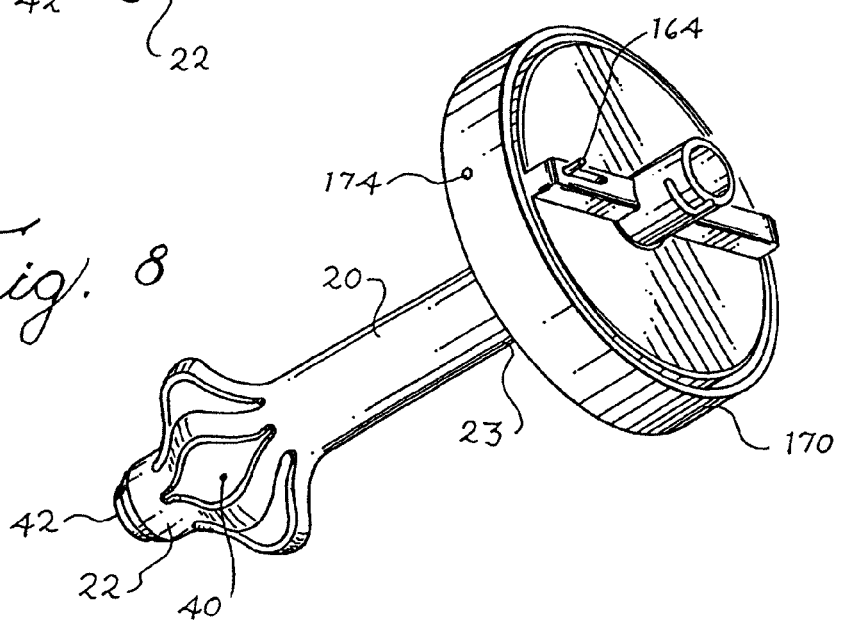
FIG. 8 is the view of FIG. 6 showing the device in a retention position.
Figure 10:
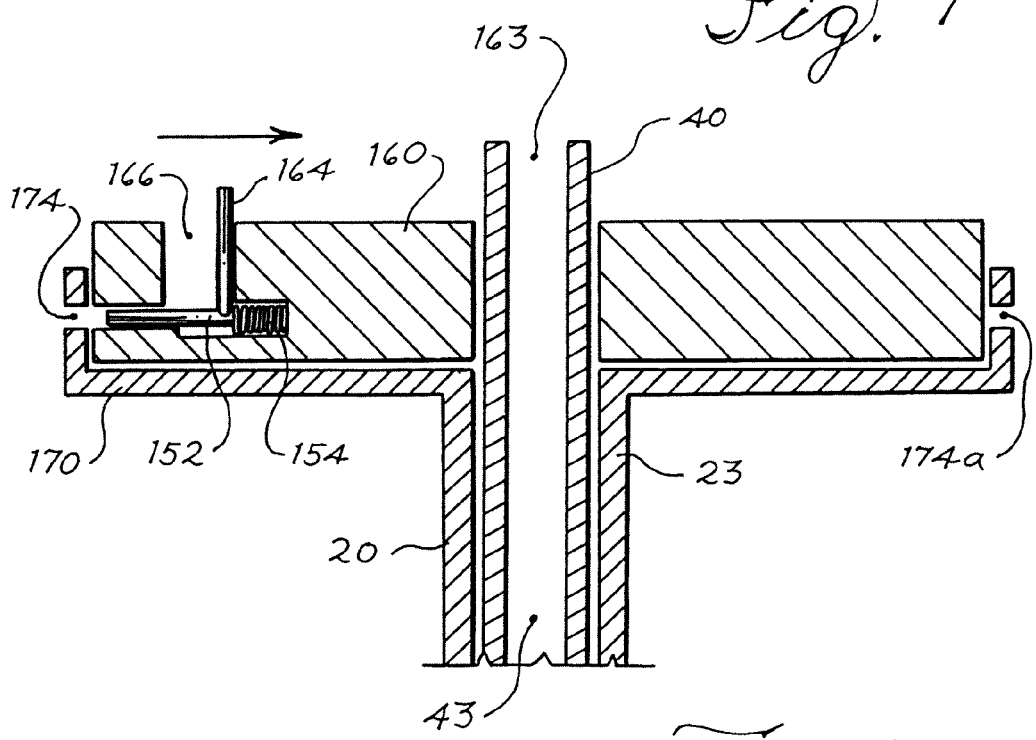
FIG. 10 is the view of FIG. 9, showing the locking device in an unlocked position.

As shown in FIGS. 9-10, pin 152 may be biased by a spring 154 to urge the pin 152 toward the aperture 174 in annulus 172. Additionally, lever 164 may extend through a slot 166 in the handle 162, with lever 164 being biased to retain pin 152 in the selected extended position. When lever 164 is moved inwardly toward the center of actuation member 160 against the biasing force of spring 154, pin 152 is forced inward within the actuation member 160 and out of aperture 174 in annulus 172. Accordingly, actuation member 160 may be rotated with respect to receiving drum 170. When lever 164 is released, pin 152 is allowed to return to its extended position through aperture 164 (or to a position where pin 152 contacts the inner surface of annulus 172 when device 100 is in an intermediate position, as shown in FIG. 7). In other embodiments, other designs may be used to remotely control the position of pin 152 with respect to aperture 174 in annulus 172.

Figure 11:
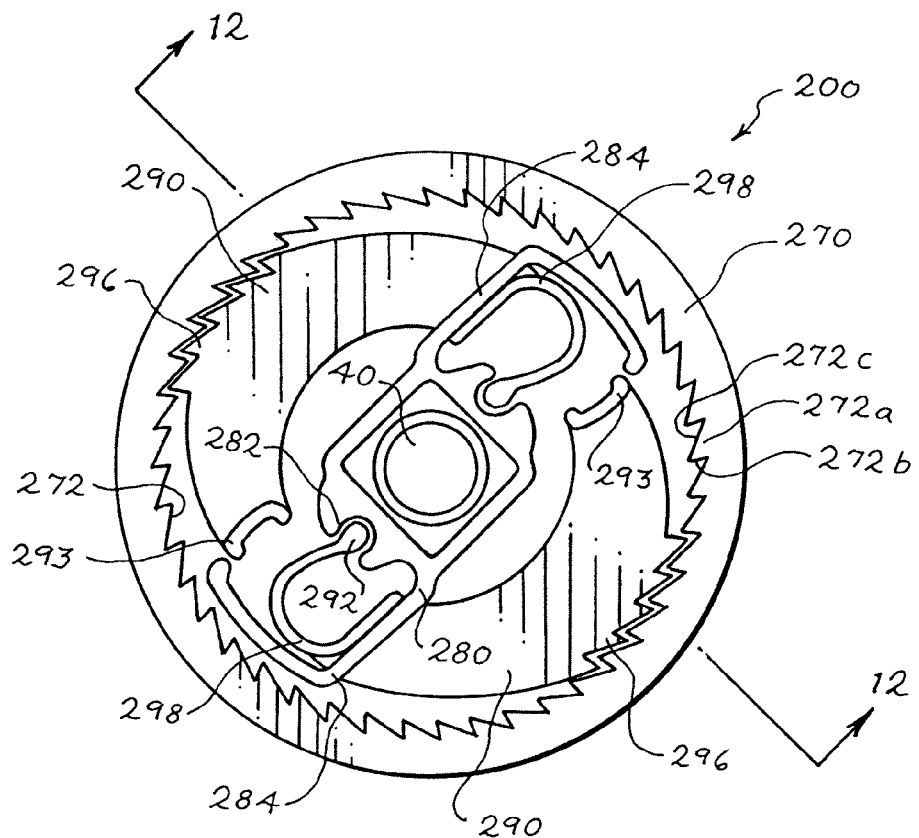
FIG. 11 is a top view of a third representative embodiment of a percutaneous insertion device showing the device in a locked position.
Figure 12:
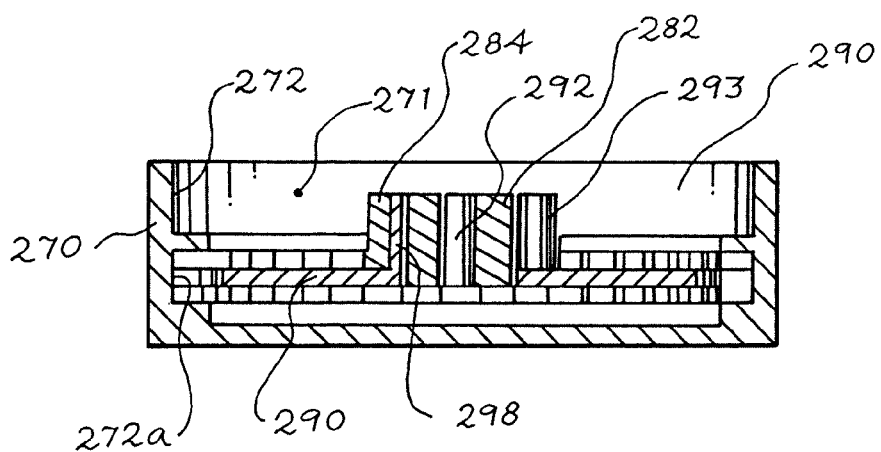
FIG. 12 is a cross-sectional view of FIG. 11 along section 12-12.
Figure 13:
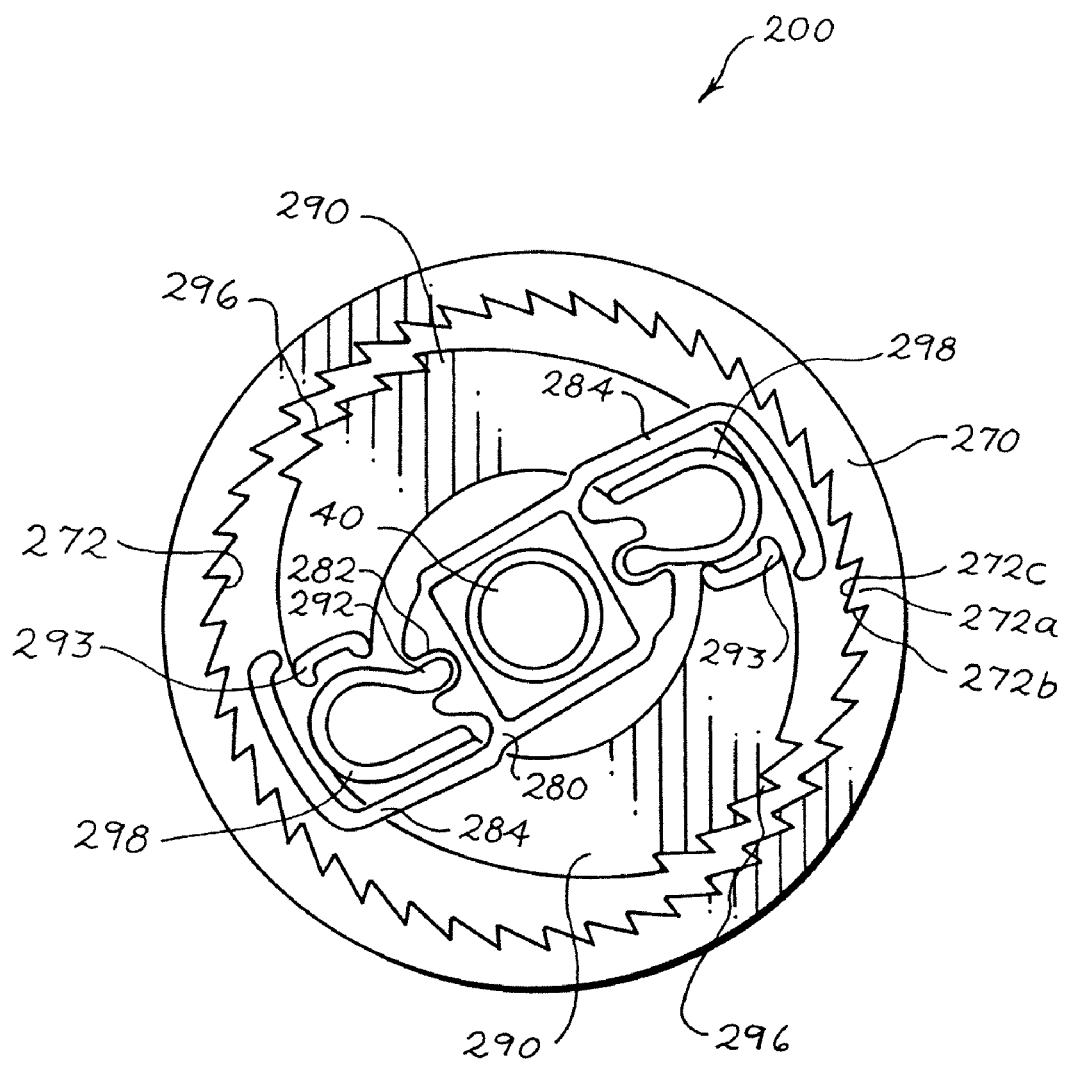
FIG. 13 is the top view of FIG. 11 showing the device in an unlocked position.

Turning now to FIGS. 11-13, a third representative embodiment of a percutaneous insertion device 200 is provided. The percutaneous insertion device 200 includes a sheath 20, a catheter 40, and arms 28 formed on sheath 20, which operate based on relative rotation between sheath 20 and catheter 40. Alternatively, sheath 520 with bulge portion 530 (530a) may be provided on device 200. The sheath 20 and catheter 40 are fixed together at fixation regions 25, 45. The sheath 20 and catheter 40 are formed and connected in the same way as discussed with respect to the first representative embodiment 10 above, and for the sake of brevity will not be repeated here.

A receiving drum 270 is provided and is fixedly connected to proximal end portion 23 of sheath 20, wherein rotation of receiving drum 270 causes similar rotation of sheath 20. Receiving drum 270 includes an inner cavity 271 that is formed by an inner surface 272 of receiving drum 270. A portion of the circumference of the inner surface 272 is formed with a plurality of ratchet teeth 272a formed around the circumference of inner surface 272. In the embodiment shown in FIGS. 11-13, each ratchet tooth 272a is formed with a first side 272b and an opposite second side 272c.

A hub 280 is fixedly engaged to the outer circumference of proximal end portion 44 of catheter 40. Accordingly, any rotation of hub 280 transfers torque to similarly rotate catheter 40. Hub 280 includes two slots 282 that receive corresponding beads 292 of one of two shoes 290. In some embodiments, slots 282 and beads 292 may be formed to limit the freedom of movement between the two components. Shoes 290 are provided within inner cavity 271. As shown in FIG. 11, a curved flexible portion 298 extends from bead 292, and is connected with the remainder of shoe 290. In some embodiments, hub 280 and shoes 290 may be formed as a single component, either integrally or monolithically, Each flexible portion 298 is biased to engage a corresponding arm 284 of the hub 280. Due to outward the biasing force of flexible portion 298, shoe 290 is biased radially outward to contact receiving drum 270. Specifically, shoes 290 include a plurality of outwardly extending ratchet teeth 296, or pawls, that are engageable with the plurality of inwardly extending ratchet teeth 272a on drum 270. The engagement between ratchet teeth 296 on shoes 290 and ratchet teeth 272a on drum 270 is normally maintained due to the outward biasing force on flexible portions 298 (as constrained by arms 284 of hub 280), which limits the outward movement of flexible portions 298.

Each shoe 290 additionally includes an upwardly extending operator portion 293 that is provided on the opposite end of shoe 290 from bead 292. Operator portion 293 provides an opposing surface on each shoe 290 that may be manipulated by the user to release the connection between ratchet teeth 296 on shoes 290 and ratchet teeth 272a on drum 270. As shown in FIG. 13, when the two operator portions 293 are compressed (typically between the user's thumb and index finger), the flexible portions 298 of each shoe 290 carry the majority of the force placed on each shoe 290 and become further compressed until each flexible portion 298 no longer contacts the corresponding arm 284 of hub 280. As flexible portions 298 are compressed, each shoe 290 translates radially inward until ratchet teeth 296 on shoe 290 no longer engage ratchet teeth 272a on drum 270. When the opposing ratchet teeth 296, 272a are disengaged, sheath 20 and catheter 40 can be rotated with respect to each other, causing arms 28 (or bulge portion 530) to operate as discussed above.

When arms 28 (or bulge portion 530) are in the selected position, operator portions 293 are released and flexible portion 298 of each shoe 290 decompresses until flexible portion 298 contacts the corresponding arm 284 of hub 280. As flexible portion 298 partially decompresses, shoes 290 extend radially outward until ratchet teeth 296 on shoes 290 reengage the corresponding ratchet teeth 272a on drum 270. With ratchet teeth 296, 272a reengaged, sheath 20 and catheter 40 can no longer rotate with respect to each other and arms 28 remain fixed in their selected orientation.

Turning now to FIGS. 14-18, a fourth representative embodiment of a percutaneous insertion device 300 is provided. This embodiment includes sheath 20, catheter 40, and arms 28 formed on sheath 20, which operate based on relative rotation between sheath 20 and catheter 40. Alternatively, sheath 520 with bulge portion 530 (530a) may be provided on device 300. As with the embodiments discussed above, catheter 40 and sheath 20 are fixed together at respective fastening regions 25, 45, allowing sheath 20 and catheter 40 to be rotated with respect to each other proximally of the respective fixation regions 25, 45. The sheath 20 and catheter 40 are formed and connected in the same way as discussed with respect to the first representative embodiment 10 above, and for the sake of brevity will not be repeated here.

Figure 17:
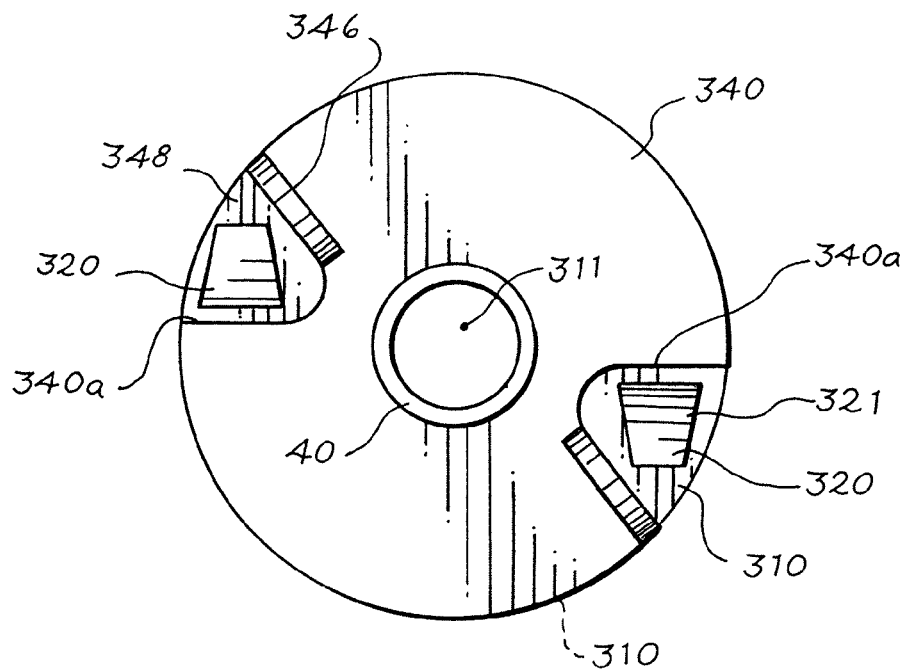
FIG. 17 is a top view of the percutaneous insertion device of FIG. 14.
Figure 18:
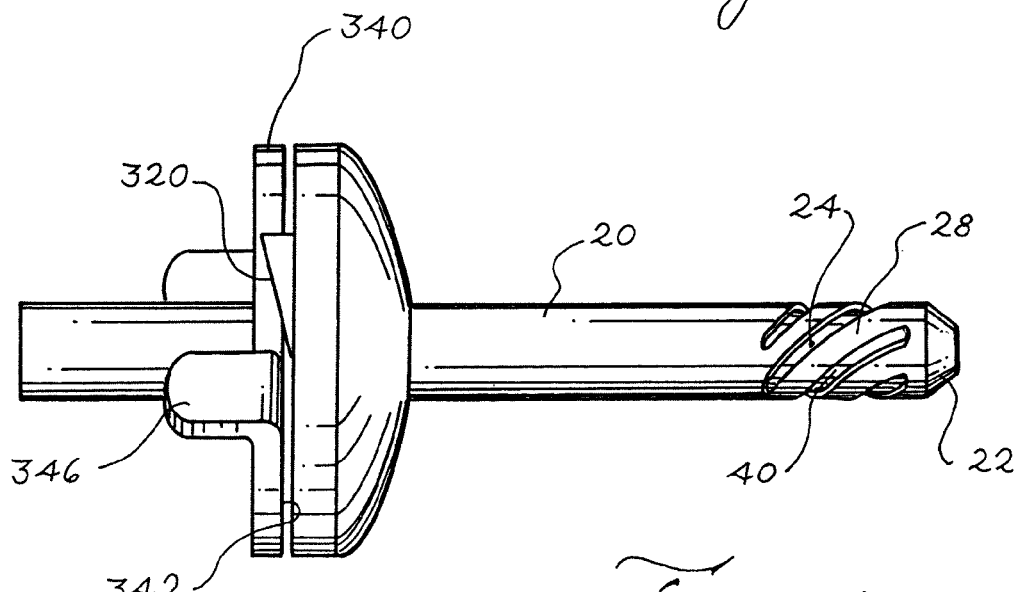
FIG. 18 is a plan view of the percutaneous insertion device of FIG. 14.

The percutaneous insertion device 300 includes a locking mechanism 302, which includes a disk 310 mounted to sheath 20 such that rotation of disk 310 causes similar and simultaneous motion of sheath 20. Percutaneous insertion device 300 additionally includes an operator 340 mounted to catheter 40 such that rotation of operator 340 causes similar and simultaneous motion of catheter 40. Disk 310 includes front and rear surfaces 312, 314 and typically is substantially half spherical. Disk 310 additionally includes at least one wedge 320 which extends from rear surface 314 of disk 310. In other embodiments, wedge 320 may be formed as a protrusion with any other suitable geometry. As shown in FIG. 17, in some embodiments, disk 310 may include two wedges 320. In embodiments with two wedges 320 inclined surfaces 321 (FIG. 16) of each wedge 320 faces opposite directions (best shown in FIGS. 14, 17). Wedge 320 may be formed monolithically with disk 310 when manufacturing disk 310, or in the alterative, wedge 320 may be manufactured separately from disk 310 and connected to disk 310 in a method that is known to those of ordinary skill in the art.

Operator 340 includes opposite first and second surfaces 342, 344. Operator 340 is positioned with respect to disk 310 such that first surface 342 of operator 340 faces rear surface 314 of disk 310. Operator 340 additionally includes at least one handle 346 that may be formed monolithically with operator 340. In some embodiments, operator 340 is manufactured with handle 346 extending perpendicularly from second surface 344 of operator 340. In other embodiments, operator 340 may be formed substantially as a flat member, with handle 346 bent backward to extend substantially perpendicularly to second surface 344, leaving a cavity 348, discussed below.

In the embodiments shown in FIGS. 14-18, operator 340 includes two handles 346 extending substantially perpendicularly from second surface 344 of operator 340. In such embodiments, handles 346 are preferably positioned on opposite sides of operator 340 and extending from second surface 344 of operator 340 substantially in parallel.

Operator 340 additionally includes at least two void spaces, or cavities, 348. In the embodiments shown in FIGS. 14-18, two void spaces 348 are provided at opposite sides of operator 340, in the proximity of each handle 346. As best shown in FIGS. 14, 16, and 17, a wedge 320 normally extends through each cavity 348 when the percutaneous insertion device 300 is in either of the insertion position or the retention position (shown in FIGS. 14 and 16, respectively). When wedge 320 extends into cavity 348, first surface 342 of operator 340 and rear surface 314 of disk 310 are in contact or in close proximity. As operator 340 is rotated in the X direction (FIG. 14) with respect to disk 310 by manipulating handle 346, first surface 342 of operator 340 contacts inclined surface 321 of wedge 320, causing operator 340 to translate away from disk 310. As shown in FIG. 15, when operator 340 is rotated with respect to disk 310 and handle 346 rotates past the corresponding wedge 320, arms 28 begin extending outwardly past the circumference of sheath 20, due to the relative rotation between sheath 20 and catheter 40, as discussed above.

With additional rotation in the X direction, edge 340a of operator 340 rotates past wedge 320, which allows wedge 320 to extend through cavity 348 in operator 340. As shown in FIG. 16, arms 28 are fully extended from sheath 20 (and percutaneous insertion device 300 is in the retention position) when wedge 320 extends through the opposite cavity 348 from which wedge 320 extended when the percutaneous insertion device 300 was in the insertion position. While the extended arms 28 bias operator 340 toward the insertion position, edge 340a of operator 340 contacts the perpendicular surface of wedge 320, preventing operator 340 from rotating with respect to disk 310 due to the rotational biasing force of extended arms 28. Accordingly, the contact between wedge 320 and edge 340a of operator 340 retains arms 28 in the extended, or locking, position shown in FIG. 16.

Arms 28 of percutaneous insertion device 300 may be transferred from the retention position to the insertion position by pulling handle 346 of operator 340 away from disk 310. This relative movement between operator 340 and disk 310 allows edge 340a of operator 340 to ride over top edge 322 (FIG. 16) of wedge 320. After edge 340a of operator 340 clears wedge 320, the user may return the percutaneous insertion device 300 to the insertion position by manipulating handle 346 to rotate operator 340 in the Y direction (FIG. 14), as aided by the biasing force of the extended arms 28 and the twisted catheter or sheath 40, 20. When operator 340 is fully rotated toward the insertion position, wedge 320 extends into the corresponding cavity 348 as shown in FIG. 14.

Turning now to FIGS. 22-31, another percutaneous insertion device 600 is provided. As with the embodiments discussed above, the percutaneous insertion device 600 may be inserted into the patient's GI tract or another portion of the patient's anatomy in accordance with conventional medical procedures. For example, during surgery the physician inserts an endoscope (not shown) or similar device through the patient's mouth or nose and into the patient's GI tract. The endoscope may be used to inflate the patient's stomach and to visualize the proper position for inserting the distal end of percutaneous insertion device 600. The physician inserts a needle and a guide wire percutaneously through the patient's abdominal wall to the position of the distal end of the endoscope. After the needle is removed, a series of dilators with increasing widths may be inserted and removed along the guide wire to increase the size of the hole, or stoma, to the outer diameter of percutaneous insertion device 600.

As best shown in FIGS. 27-28, an insertion dilator 690 is inserted through lumen 608 of percutaneous insertion device 600 and may be inserted into the patient along with the percutaneous insertion device 600. When the insertion dilator 690 is inserted with the insertion device 600, a mating portion 694 of the insertion dilator 690 is engaged with a corresponding non-circular portion 608a of the catheter 610 of the percutaneous insertion device 600 (discussed below and shown in FIG. 24). The distal end 691 of the insertion dilator 690 includes a gradually expanding tip portion 691a that extends from a distal end portion 612 of the catheter 610 and is configured to minimize discomfort and tissue damage as the insertion dilator 690 and the catheter 610 are inserted into the anatomy.

The proximal end 692 of the insertion dilator 690 includes a handle 698 that extends from the catheter 610 when the insertion dilator 690 is inserted therein that provides structure for the user to manipulate to provide torque along the length of the insertion dilator 690. The insertion dilator 690 additionally includes a junction 695 that provides a transition between the cylindrical distal end portion 691 and the mating portion 694, which is formed with a non-circular cross-section sized and shaped to engage and transfer torque to the non-circular portion 608a of the catheter 610.

When inserting the insertion dilator 690 and the catheter 610 into the patient, a proximal end of the wire guide may be threaded through an aperture 699 on the distal end 691 of the insertion dilator 690. The catheter 610 and insertion dilator 690 (inserted through a lumen 608 of the catheter 610) are then inserted through the stoma and positioned into the desired position within the patient. When inserting the catheter 610 and the insertion dilator 690, a bulge portion 620 of the catheter 610 is held in a narrowed position (FIG. 26, discussed below. FIG. 26 shows the catheter 610 in the narrowed position due to the insertion of an operator 710, discussed below, with the bulge portion 620 narrowed due to relative rotation between the two members. The structure and operation of the insertion dilator 690 to maintain the catheter 610 in the narrowed position is representative of this figure). In the narrowed position, the bulge portion 620 is narrowed or compressed to be substantially the same diameter as the central portion 616, or another portion, of the catheter 610. Once the percutaneous insertion device 600 is correctly positioned, the bulge portion 620 is extended to the extended position (FIG. 27), as discussed below, by releasing the relative rotation between the catheter 610 and the insertion dilator 690. The endoscope, insertion dilator 690, and the wire guide may then be removed from the patient.

As best shown in FIGS. 22 and 24-26, the percutaneous insertion device 600 includes an elongate catheter 610 that extends between a distal end portion 612 and a proximal end portion 614 and defines a lumen 608 therethrough for the passage of liquid. A central portion 616 is defined between the distal and proximal end portions 612, 614. The catheter 610 is configured to extend through the stoma and into a portion of the GI tract to supply nutrients thereto. Alternatively, the catheter 610 may be configured with an alternate profile to line the stoma and be retained in place in another portion of the anatomy with the movable bulge portion 620 disposed within the patient just inside the stoma. A tube (similar to tube 90 of FIG. 1 discussed above) may be connected to a proximal end portion 614 of the catheter 610 to provide flow to or receive flow from proximal end portion 614 of catheter 610.

Catheter 610 may be formed from a sufficiently flexible but strong material such as silicone, polyurethane, or known co-polymers of these materials, such that catheter 610 may be twisted along its longitudinal axis 610a (shown in FIG. 22). Catheter 610 defines a lumen 608 along the length of catheter 610 that is sized to allow sufficient nutrient (or other liquid) flow to the GI tract or other portion of the anatomy, while minimizing the outer diameter of the catheter 610 to minimize patient discomfort, required stoma size, and tissue damage when the percutaneous insertion device 600 is installed.

Distal end portion 612 of catheter 610 may be formed with a narrowed cone-shaped end, which provides for gradual expansion of the tissue that the catheter 610 is inserted therethrough, which minimizes patient discomfort and damage to surrounding tissue during installation in conjunction with the insertion dilator 690. Lumen 608 includes a non-circular portion 608a as best shown in FIGS. 23-25. The internal diameter D1 (FIG. 24) of the non-circular portion 608a is smaller than the internal diameter D2 of the lumen 608 along the remainder of the catheter 610 between the non-circular portion 608a and proximal end portion 614. In some embodiments, the non-circular portion 608a is defined within the distal end portion 612, while in other embodiments the non-circular portion 608a may be disposed in other portions of the catheter 610.

A possible square cross-sectional geometry of the non-circular portion 608a of the catheter 610 is shown in FIG. 23. Alternatively, the non-circular portion 608a may be rectangular, triangular, hexagonal, octagonal, or with any other shape that has flat (or non-circular) surfaces that are configured to engage a corresponding surface defined in a mating portion 706 of an insertion member 700 (collectively the insertion dilator 690 and an operator 710, discussed below). Specifically, the matching shapes of the non-circular portion 608a and the mating portion 706 should be sized and shaped to provide sufficient engagement surfaces to prevent relative rotation between the catheter 610 and the insertion member 700 at the point of engagement between the non-circular portion 608a and the mating portion 706, while maximizing the cross-sectional area within the non-circular portion 608a of the lumen 608 available for flow to minimize head loss therethrough. In other embodiments, the non-circular portion 608a may be formed with other non circular cross-sections that substantially prevent relative rotation between the catheter 610 and the insertion member 700 at the point of engagement between the non-circular portion 608a and the mating portion 694.

Additionally, a non-circular portion 608a with a plurality of similar edges along the inner circumference of the lumen 608 maximizes the engagement between the insertion member 700 and the catheter 610 with different rotational positions of each member. In other words, a non-circular portion 608a formed as a hexagon (i.e. with six flat edges normally at substantially 60 degree angles from neighboring edges) may be preferred to a non-circular portion 608a with a triangular cross-section (i.e. with three flat edges normally at substantially 120 degree angles from neighboring edges) at least with respect to this attribute of the selection of the cross-section because the hexagonal cross-section allows for engagement between the non-circular portion 608a and the mating portion 694 in six different relative positions of the two members with respect to each other, while a triangular cross section allows for engagement at three different relative positions.

Alternatively, a cross-sectional orientation with fewer, but longer, flat or non-circular surfaces, and larger angles between neighboring flat surfaces (i.e. a cross-section formed as a triangle as compared to a hexagon) may be beneficial because a stronger rigid connection between the catheter 610 and the insertion device 700 (at the non-circular portion 608a and the mating portion 694) may be possible. White these attributes that may be considered in the determination of the preferred cross-section of the non-circular portion 608a, one of ordinary skill in the art will understand that other design parameters, such as manufacturability, strength, and cost, will also be determinative as to which specific non-circular cross-section is appropriate for each application.

The distal end portion 612 of the catheter 610 may additionally include a bulge portion 620 that is formed proximate the non-circular portion 608a and between the non-circular portion 608a and the proximal end portion 614. In other embodiments, the bulge portion 620 may be disposed in another portion of the catheter 610 between the non-circular portion 608a and the proximal end portion 614. For example, the bulge portion 620 may be disposed in the central portion 616 or proximate the proximal end portion 614. The proper position of the bulge portion 620 is based on the intended use of the percutaneous insertion device 600 within the patient, and more specifically where the tissue or other anatomical structure is located (with respect to the stoma or other entry point into the patient) that is suitable for being anchored to by the bulge portion 620.

As shown in FIGS. 29-31, the bulge portion 620 may be formed with a substantially continuous outer surface around the circumference of the bulge portion 620 that is biased to be normally expanded radially beyond the outer circumference of the central portion 616 or other remaining portions of the catheter 610 between the non-circular portion 608a and the proximal end portion 614. The bulge portion 620 may include an outer surface 623 that encloses a substantially hollow interior portion to prevent fluid communication between the lumen 608 and the outside of the bulge portion 620.

Alternatively, as shown in FIGS. 22 and 24-27, the bulge portion 620 may be formed with a plurality of parabolic arms 630 that are biased to extend radially outward from the circumference of distal end portion 612 of catheter 610. The plurality of arms 630 are defined by slots 634 that are disposed between neighboring arms 630. As best shown in FIG. 22, the plurality of arms 630 define a plurality of spaces 635 between neighboring arms 630 when the bulge portion 620 is biasingly aligned in its normal extended position. As shown in FIG. 31, in some embodiments a flexible cover 631 (shown in the figure with a portion of the cover 631 removed to show the plurality of arms 630 thereunder) is fixed to the catheter 610 over the plurality of arms 630 and expands and contracts with the movement of the plurality of arms 630 to prevent fluid communication from the lumen 608 through the spaces 635 and out of the catheter 610.

Bulge portion 620 may include a plurality of springs that are normally biased to radially extend bulge portion 620 beyond the outer circumference of the catheter 610. Alternatively, bulge portion 620 may be formed with a naturally resilient material that is shaped to be naturally biased outward away from catheter 610, but capable of compressing toward the outer diameter of the catheter 610 when the catheter 610 is twisted along its length (discussed below). In other embodiments, bulge portion 620 may be formed with other geometries that are biased outward from the remaining outer circumference of catheter 610 by compressible toward the circumference of the catheter 610.

Catheter 610 is made from a relatively flexible material that can be shaped or bent into various angles along the length of the catheter 610 to allow for insertion and placement into a large array of potential locations within a patient. Catheter 610 is additionally sized with relatively thin walls that allow catheter 610 to be twisted along its length with the proximal end portion 614 rotating a significant arc length with respect to the distal end portion 612.

Bulge portion 620 is configured to narrow (i.e. compress toward the outer diameter of the other portions of the catheter 610, such as the central portion 616) as the catheter 610 is twisted along its length because the bulge portion 621 is inherently less resistant to torsion than the remainder of the catheter 610 due to its geometry and orientation. In embodiments where the bulge portion includes a plurality of arms 630, the arms 630 transfer from the normal parabolic shape (FIG. 22), or other extending shape, and substantially parallel to the longitudinal axis 610a of the catheter 610 to an orientation that closely matches the circumference of the central portion 616 of the catheter 610 with the arms 630 each disposed at an oblique angle θ (FIG. 26) with respect to the longitudinal axis 610a of the catheter 610.

Accordingly, as torque is applied to the length of the catheter 610, the majority of the torsional stress is relieved by the twisting of the bulge portion 620. As the bulge portion 620 twists, the outer diameter of the bulge portion 620 necessarily reduces toward the diameter of the central portion 616, or another portion, of the catheter 610. With sufficient rotation, the bulge portion 620 narrows to substantially the same diameter of the catheter 610, which allows the catheter 610 to be freely inserted or withdrawn from the stoma and/or the final position of the catheter 610 within the patient.

The bulge portion 620 restores to the extended position when the torque on the catheter 610 is released due to the bias imparted onto the bulge portion 620. When the catheter 610 is positioned within a patient, the full restoration of the bulge portion 620 to the extended position may be impeded by surrounding tissue, which substantially fixes the catheter 610 into the proper position within the patient.

The non-circular portion 608a is adapted to receive and engage a corresponding mating portion 706 of an insertion member 700 within the lumen 608 of the catheter 610. The insertion member 700 may be the insertion dilator 690 (discussed above) which is used both to engage the non-circular portion 608a of the catheter 610 and transfer the bulge portion 620 to the narrowed position due to torque applied between the insertion member 700 and the catheter 610, as well as to properly position and align the catheter 610 within the patient, as discussed above.

Alternatively as shown in FIGS. 22 and 25-26, the insertion member 700 may be an operator 710 that is configured to be inserted into lumen 608 through the proximal end portion 614 of the catheter 610. The operator 710 includes a mating portion 706 for engaging the non-circular portion 608a of the catheter 610. The operator 710 extends between a distal end portion 712 and a proximal end portion 714. The mating portion 706 is disposed between the distal and proximal end portions 712, 714 and is configured to engage the non-circular portion 608a and transfer torque thereto. Preferably, the mating portion 716 is proximate the distal end portion 712 to prevent the distal end portion 712 from extending through the distal end aperture 612a of the catheter 610 when the mating portion 706 engages the non-circular portion 608a but the mating portion 706 may be disposed in other positions of the operator 710 as necessary to engage the catheter 610. The operator 710 normally does not extend through the distal end aperture 612a of the catheter 610.

The operator 710 is used to narrow the bulge portion 620 to allow the catheter 610 to be removed from the patient when the catheter 610 has been properly positioned within the patient. Similar to the insertion dilator 690, the operator 710 includes a handle 719, or similar structure, that is disposed on the proximal end of the operator 710 and provides structure for the user to hold for the application of torque thereto when the mating portion 706 is engaged with the non-circular portion 608a.

As discussed above, the insertion member 700 (i.e. the insertion dilator, the operator 710, or other similar structure) should be sufficiently flexible to allow navigation though the lumen 608 of the catheter 610 when inserted into the patient, but include a substantially greater strength or resistance to twisting than the catheter 610 to ensure that the catheter 610, and more specifically the bulge portion 620, twists when a torque is applied between the catheter 610 and the insertion member 700.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A medical device comprising:
   (a) a substantially tubular hollow catheter having a distal end portion and a proximal end portion;
   (b) a sheath disposed coaxially about the catheter, the sheath comprising:
      (i) a distal end portion and a proximal end portion, wherein the distal end portion of the sheath is substantially fixed to the catheter at a fixation point to prevent relative rotation between the catheter and the sheath at the fixation point,
      (ii) a plurality of arms defined in the sheath proximally of the fixation point, wherein the plurality of arms are each provided in parallel and at an oblique angle to a longitudinal axis of the sheath, and the first ends of each of the plurality of arms are provided at equal distances from adjacent slots around the circumference of the sheath;

(c) an actuatable member provided on one of the proximal end portion of the sheath or the proximal end portion of the catheter to provide relative rotation between the sheath and the catheter proximally of the fixation point;

wherein the actuatable member comprises a first handle that extends radially from the proximal end portion of either the sheath or the catheter;

wherein the other of the sheath or the catheter further comprises a second handle that extends radially from the proximal end portion of the other of the sheath or the catheter and includes a latch; and wherein rotation of the proximal end portion of the sheath relative to the proximal end portion of the catheter causes the plurality of arms to extend radially outward.

2. The medical device of claim 1, wherein the region of the sheath with the plurality of arms is substantially the same circumference as the proximal end portion of the sheath when the sheath and the catheter are not rotated relative to each other.

3. The medical device of claim 1, wherein each of the plurality of arms form an arch that extends radially outward to have a larger circumference than the proximal end portion of the sheath when the sheath and the catheter are rotated with respect to each other.

4. The medical device of claim 1, wherein the first handle may be rotated with respect to the second handle to engage the second handle to retain the plurality of arms radially extended beyond the circumference of the proximal end portion of the sheath.

5. A medical device comprising:
(a) a substantially tubular hollow catheter having a distal end portion and a proximal end portion;
(b) a sheath disposed coaxially about the catheter, the sheath comprising:
(i) a distal end portion and a proximal end portion, wherein the distal end portion of the sheath is substantially fixed to the catheter at a fixation point to prevent relative rotation between the catheter and the sheath at the fixation point,
(ii) a plurality of arms defined in the sheath proximally of the fixation point, wherein the plurality of arms are each provided in parallel and at an oblique angle to a longitudinal axis of the sheath, and the first ends of each of the plurality of arms are provided at equal distances from adjacent slots around the circumference of the sheath;
(c) an actuatable member provided on one of the proximal end portion of the sheath or the proximal end portion of the catheter to provide relative rotation between the sheath and the catheter proximally of the fixation point;
wherein the actuatable member comprises a disk that extends from the proximal end portion of the catheter,
wherein the sheath further comprises a drum that extends from the proximal end portion of the sheath and substantially surrounds an outer circumference of the disk,
wherein the disk is rotatable with respect to the drum, and
wherein rotation of the proximal end portion of the sheath relative to the proximal end portion of the catheter causes the plurality of arms to extend radially outward.

6. A medical device comprising:
(a) a substantially tubular hollow catheter having a distal end portion and a proximal end portion;
(b) a sheath disposed coaxially about the catheter, the sheath comprising:
(i) a distal end portion and a proximal end portion, wherein the distal end portion of the sheath is substantially fixed to the catheter at a fixation point to prevent relative rotation between the catheter and the sheath at the fixation point,
(ii) a plurality of arms defined in the sheath proximally of the fixation point, wherein the plurality of arms are each provided in parallel and at an oblique angle to a longitudinal axis of the sheath, and the first ends of each of the plurality of arms are provided at equal distances from adjacent slots around the circumference of the sheath;
(c) an actuatable member provided on one of the proximal end portion of the sheath or the proximal end portion of the catheter to provide relative rotation between the sheath and the catheter proximally of the fixation point;
wherein the actuatable member is provided on the catheter and includes a handle and a first edge,
wherein the medical device further comprises a disk extending from the sheath comprising a first protrusion that is selectively engageable with the first edge, and
wherein rotation of the proximal end portion of the sheath relative to the proximal end portion of the catheter causes the plurality of arms to extend radially outward.

7. The medical device of claim 6, further comprising a second edge on the actuatable member and a second protrusion on the disk, wherein the first protrusion engages the first edge when the catheter is in a first position with respect to the sheath, and the second protrusion engages the first edge when one of the catheter or the sheath is rotated with respect to the other of the catheter or the sheath such that the arms are fully extended radially outward from the proximal end of the sheath.

8. The medical device of claim 7, wherein the catheter is retained at the selected position with respect to the sheath when the second protrusion engages the first edge.

9. The medical device of claim 7, wherein the first and second edges are disposed at substantially opposite sides of the actuatable member and the first and second protrusions are aligned at substantially opposite sides of the disk.

10. A medical device comprising:
(a) a substantially tubular hollow catheter having a distal end portion and a proximal end portion;
(b) a sheath disposed coaxially about the catheter, the sheath comprising:
(i) a distal end portion and a proximal end portion, wherein the distal end portion of the sheath is substantially fixed to the catheter at a fixation point to prevent relative rotation between the catheter and the sheath at the fixation point,
(ii) a plurality of arms defined in the sheath proximally of the fixation point, wherein the plurality of arms are each provided in parallel and at an oblique angle to a longitudinal axis of the sheath, and the first ends of each of the plurality of arms are provided at equal distances from adjacent slots around the circumference of the sheath;
(c) an actuatable member provided on one of the proximal end portion of the sheath or the proximal end portion of the catheter to provide relative rotation between the sheath and the catheter proximally of the fixation point;
wherein the actuatable member comprises a plurality of shoes with radially outward extending teeth, wherein the teeth are engageable with similar inwardly extending teeth disposed on a drum provided on the opposite of the sheath or the catheter, and wherein rotation of the proximal end portion of the sheath relative to the proximal end portion of the catheter causes the plurality of arms to extend radially outward.

11. The medical device of claim 1, wherein the medical device is configured to be inserted percutaneously through the abdomen or stomach of a mammal.

12. The medical device of claim 1, wherein the medical device is configured to percutaneously deliver nourishment to a mammal.

13. The medical device of claim 1, wherein the plurality of arms are defined by a plurality of slots that are formed in the sheath at the edges between neighboring slots.

14. The medical device of claim 5, wherein the medical device is configured to be inserted percutaneously through the abdomen or stomach of a mammal.

15. The medical device of claim 5, wherein the medical device is configured to percutaneously deliver nourishment to a mammal.

16. The medical device of claim 5, wherein the plurality of arms are defined by a plurality of slots that are formed in the sheath at the edges between neighboring slots.

17. The medical device of claim 6, wherein the medical device is configured to be inserted percutaneously through the abdomen or stomach of a mammal.

18. The medical device of claim 6, wherein the medical device is configured to percutaneously deliver nourishment to a mammal.

19. The medical device of claim 6, wherein the plurality of arms are defined by a plurality of slots that are formed in the sheath at the edges between neighboring slots.

20. The medical device of claim 10, wherein the medical device is configured to be inserted percutaneously through the abdomen or stomach of a mammal.

21. The medical device of claim 10, wherein the medical device is configured to percutaneously deliver nourishment to a mammal.

22. The medical device of claim 10, wherein the plurality of arms are defined by a plurality of slots that are formed in the sheath at the edges between neighboring slots.

* * * * *